(12) United States Patent
Parthemore et al.

(10) Patent No.: US 12,290,365 B1
(45) Date of Patent: May 6, 2025

(54) HEALTH AND SAFETY MONITORING AND ALERT SYSTEM AND METHOD

(71) Applicant: TRITON SENSORS, LLC, Harrisburg, PA (US)

(72) Inventors: Lance Parthemore, Harrisburg, PA (US); Garrison Parthemore, Harrisburg, PA (US); Jack Guerrisi, Harrisburg, PA (US); Mauricio Solis, Edinburg, TX (US); William Wendin, Carnelian Bay, CA (US)

(73) Assignee: TRITON SENSORS, LLC, Harrisburg, PA (US)

( * ) Notice: Subject to any disclaimer, the term of this patent is extended or adjusted under 35 U.S.C. 154(b) by 0 days.

(21) Appl. No.: 18/929,010

(22) Filed: Oct. 28, 2024

Related U.S. Application Data

(60) Provisional application No. 63/656,994, filed on Jun. 6, 2024.

(51) Int. Cl.
| | |
|---|---|
| *G16H 40/63* | (2018.01) |
| *A61B 5/18* | (2006.01) |
| *G16H 40/67* | (2018.01) |

(52) U.S. Cl.
CPC .............. *A61B 5/18* (2013.01); *G16H 40/63* (2018.01); *G16H 40/67* (2018.01)

(58) Field of Classification Search
CPC ........... A61B 5/18; G16H 40/67; G16H 40/63
USPC .......................................................... 340/540
See application file for complete search history.

(56) References Cited

U.S. PATENT DOCUMENTS

| | | | | | |
|---|---|---|---|---|---|
| 7,466,224 | B2* | 12/2008 | Ward | ................. | G08B 13/2454 340/540 |
| 7,535,353 | B2* | 5/2009 | Hirai | ..................... | G06V 20/52 340/609 |
| 12,205,718 | B2* | 1/2025 | Derdzinski | ............ | G16H 40/67 |
| 2009/0135007 | A1* | 5/2009 | Donovan | .............. | H04L 41/069 340/500 |
| 2010/0321184 | A1* | 12/2010 | Dreuillet | ................. | G01S 13/56 340/540 |
| 2014/0327543 | A1* | 11/2014 | Showen | .................... | G01S 5/18 340/540 |
| 2023/0196900 | A1* | 6/2023 | Kelly | .................. | G08B 21/245 340/540 |

* cited by examiner

*Primary Examiner* — Naomi J Small
(74) *Attorney, Agent, or Firm* — McNees Wallace & Nurick LLC

(57) ABSTRACT

A health and safety monitoring and alert system includes a main system and a detection system. The main system includes a processor, a storage medium, and a visualization system. The detection system is configured to detect health and safety information relating to occupants in a space and communicate the detected health and safety information with the main system by a network connection. The visualization system includes a display interface, and the display interface is configured to represent the health and safety information by at least one of using symbols, numbers, or colors.

30 Claims, 14 Drawing Sheets

HEALTH AND SAFETY MONITORING AND ALERT SYSTEM AND METHOD

CROSS-REFERENCE TO RELATED APPLICATIONS

This application claims priority to and the benefit of U.S. Provisional Application No. 63/656,994, filed Jun. 6, 2024, which is hereby incorporated by reference in its entirety.

FIELD OF DISCLOSURE

The present disclosure relates to a health and safety monitoring and alert system and method thereof.

BACKGROUND

Many establishments need to be monitored to ensure safety and health of their customers, clients, patrons, employees, etc. These establishments may include educational institutions, businesses, or even private residences, including homes. To provide safe and healthy environments, it is essential to detect and prevent certain unwanted behaviors or undesirable conditions.

Detection can be achieved by monitoring a space within an establishment. Deploying personnel, such as security staff, to monitor a space may be considered. This approach allows security personnel to detect, prevent, mitigate, or eliminate unwanted behaviors or undesirable conditions in the monitored space. However, in some cases, deploying personnel may not be feasible or cost-effective, and it may not be suitable for certain spaces, such as, restrooms, locker rooms, fitting rooms, or bedrooms, where monitoring would invade privacy.

Installing security devices may also be considered for monitoring and detection. This approach is often both feasible and cost-effective. Nonetheless, in many areas, installing certain security devices, such as visual surveillance devices or cameras, would invade individuals' privacy. Without visual information, detecting unwanted behaviors or undesirable conditions may not be sufficient to respond promptly and prevent or mitigate these issues, as it becomes challenging to recognize the precise status of the monitored space.

Therefore, there remains a need to provide a health and safety monitoring and alert system and method that can reliably and accurately monitor and detect unwanted behaviors or undesirable conditions in a monitored space in a privacy compliant manner and alert the detection of such behaviors or conditions.

SUMMARY

The present disclosure describes various exemplary embodiments of a health and safety monitoring and alert system and method thereof.

In an exemplary embodiment, a method of monitoring health and safety information of a space in a privacy compliant manner provides a detection system and a main system. The detection system includes a presence detection module. The main system includes a visualization system including a display interface. The detection system detects signals in a space. The detection system analyzes the signals and determines presence of a human in the space. The detection system detects occupancy information. The detection system and the main system communicate the occupancy information. The occupancy information includes one or more of (i) a number of occupants in the monitored space; (ii) a duration time of each occupant remaining in the monitored space; (iii) a location of each occupant being located in the monitored space; (iv) entrance of an occupant into the monitored space; (v) a departure of an occupant from the monitored space; (vi) a number of occupants entered into the monitored space; (vii) a number of occupants exiting the monitored space; and (viii) an average number of occupants in the monitored space in a certain time range. The visualization system represents the occupancy information on the display interface by using at least one of symbols, numbers, or colors.

In another exemplary embodiment, a health and safety monitoring and alert system includes a main system and a detection system. The main system includes a processor configured to communicate health and safety information relating to occupants in a space; a readable and writable storage medium communicatively coupled to the processor and storing instructions that are executable by the processor; and a visualization system configured to communicate with the processor. The visualization system includes a display interface. The detection system includes a controller coupled to a module configured to detect health and safety information relating to occupants in a space. The controller includes a controller processor and a readable and writeable controller storage medium communicatively coupled to the controller processor and storing instructions that are executable by the controller processor. The module includes a presence detection module configured to detect human presence in the space. The display interface is configured to represent the detected health and safety information by using at least one of symbols, numbers, or colors in a privacy compliant manner. The health and safety information includes occupancy information, and the occupancy information including one or more of: (i) a number of occupants in the monitored space; (ii) a duration time of each occupant remaining in the monitored space; (iii) a location of each occupant being located in the monitored space; (iv) entrance of an occupant into the monitored space; (v) a departure of an occupant from the monitored space; (vi) a number of occupants entered into the monitored space; (vii) a number of occupants exiting the monitored space; and (viii) an average number of occupants in the monitored space in a certain time range. The detection system is configured to communicate the detected health and safety information with the main system by a network connection.

In another example, a health and safety monitoring and alert system includes a main system and a detection system. The main system includes a processor configured to communicate health and safety information relating to occupants in a space; a readable and writable storage medium communicatively coupled to the processor and storing instructions that are executable by the processor; and a visualization system configured to communicate with the processor. The visualization system including a display interface. The detection system includes a controller coupled to a module configured to detect health and safety information relating to occupants in a space. The controller includes a controller processor and a readable and writeable controller storage medium communicatively coupled to the controller processor and storing instructions that are executable by the controller processor. The module includes (i) a presence detection module, (ii) a noise detection module, and (iii) an air quality detection module. The presence detection module is configured to detect presence of occupants in the space. The presence detection module includes a thermal module configured to detect heat emitted by the occupants in order to obtain occupancy information. The occupancy information includes one or more of: a number of occupants in the monitored space; a duration time of each occupant remaining in the monitored space; and a location of each occupant being located in the monitored space. The noise detection module includes a microphone configured to detect predetermined sounds in the space and a filter. The predetermined sounds include at least one of screaming, shouting, glass breaking sounds, gunshots, tamper sounds, words, or emergency keywords. The air quality detection module is configured to detect predetermined particulate matter or airborne chemicals in the space. The display interface is configured to represent the detected health and safety information by using at least one of symbols, numbers, or colors. The detection system is configured to communicate the detected health and safety information with the main system by a network connection.

In another example, a health and safety monitoring and alert system includes a main system and a detection system. The main system includes a processor configured to communicate health and safety information relating to occupants in a space; a readable and writable storage medium communicatively coupled to the processor and storing instructions that are executable by the processor; and a visualization system configured to communicate with the processor. The visualization system including a display interface. The detection system includes a controller coupled to a module configured to detect health and safety information relating to occupants in a space. The controller includes a controller processor and a readable and writeable controller storage medium communicatively coupled to the controller processor and storing instructions that are executable by the controller processor. The module includes (i) a presence detection module, (ii) a noise detection module, and (iii) an air quality detection module. The presence detection module is configured to detect presence of occupants in the space. The presence detection module includes a Bluetooth module configured to detect Bluetooth signals from mobile devices in order to obtain occupancy information. The occupancy information includes one or more of: a number of occupants in the monitored space; a duration time of each occupant remaining in the monitored space; and a location of each occupant being located in the monitored space. The noise detection module includes a microphone configured to detect predetermined sounds in the space and a filter. The predetermined sounds include at least one of screaming, shouting, glass breaking sounds, gunshots, tamper sounds, words, or emergency keywords. The air quality detection module is configured to detect predetermined particulate matter or airborne chemicals in the space. The display interface is configured to represent the detected health and safety information by using at least one of symbols, numbers, or colors. The detection system is configured to communicate the detected health and safety information with the main system by a network connection.

Other features and advantages of the present invention will be apparent from the following more detailed description of exemplary embodiments, taken in conjunction with the accompanying drawings, which illustrates, by way of example, the principles of the invention.

BRIEF DESCRIPTION OF THE DRAWINGS

Wherever possible, the same reference numbers will be used throughout the drawings to represent the same parts.

DETAILED DESCRIPTION

The present disclosure provides a health and safety monitoring and alert system and method that can reliably and accurately monitor and detect unwanted behaviors or undesirable conditions in a monitored space in a privacy compliant manner and alert the detection of such behaviors or conditions. More specifically, the present disclosure provides a health and safety monitoring and alert system and method encompassing a visualization system and method that will report detected behaviors or conditions to a user of the system so that the system facilitates and allows the user to take action to remove or prevent such behaviors or conditions.

Additionally, the present disclosure aims to provide a modularized detection and monitoring system such that a user of the system can elect and configure the system in accordance with unwanted behaviors and/or undesirable conditions subject to monitoring. There may be different unwanted behaviors and/or undesirable conditions a user of the system desires to monitor and detect to ensure safety and health in their establishment.

Figure 1:
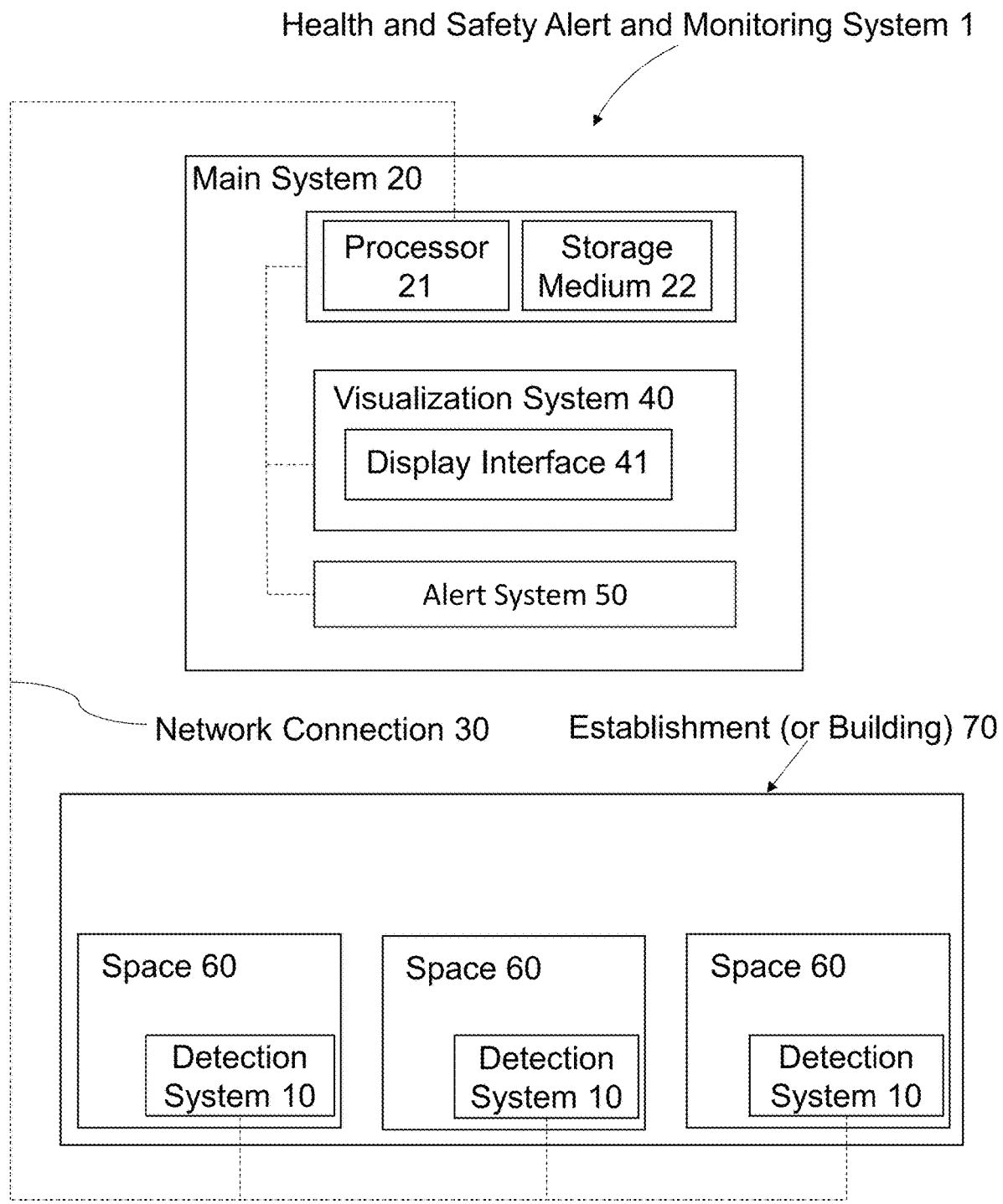
FIG. 1 shows a schematic representation of an exemplary health and safety monitoring and alert system.

Referring to FIG. 1, in some implementations, a health and safety monitoring and alert system 1 includes a detection system 10 and a main system 20 to monitor a space 60 in an establishment 70 (e.g., premises or a building). The detection system 10 and main system 20 communicate by a network connection 30, e.g., wires, or wired or wireless network connections. In some implementations, the detection system 10 and the main system 20 may communicate by any wireless communication protocols or means, such as Bluetooth, Wi-Fi, RF transmission, GPS, ZigBee, Z-Wave, or the like. The system 1 may monitor more than one space 60 in the establishment 70.

In some implementations, the health and safety monitoring and alert system 1 may include one detection system 10 coupled to one main system 20 or more than one detection system 10 coupled to one or more main systems 20. The main system 20 may be configured as a network-based management platform or cloud management platform. The main system 20 may not need to be physically located within the establishment 70. In this case, the main system 20 is located at a disparate location and communicatively connected, such as in a cloud computing system.

The detection system 10 monitors and detects unwanted behaviors and/or undesirable conditions in the space 60, including one or more modules for such monitoring and detection. Such modules may include a presence detection module, an air quality detection module, and a noise detection module, or combinations thereof, which will be described in detail later. To avail the privacy concerns with most systems, the present system 1 does not monitor or detect information that would invade the privacy of occupants 80 in the monitored space 60, e.g., video surveillance—while providing visualization of monitoring and detection so that a user of the system 1 can ensure safety and health in their establishment 70 effectively and accurately.

The main system 20 includes a processor 21, a storage medium 22, and a visualization system 40. The processor 21 is configured for communicating between the detection system 10 and the storage medium 22. The processor 21 may receive information from the detection system 10 and process the information via execution of instructions. The storage medium 22 may include a readable and writable storage medium communicatively coupled to the processor 21 and storing instructions that are executable by the processor 21. In some implementations, the main system 20 may be configured to support and control the detection system 10. In some implementations, the user of the system 1 may store physical information about monitored spaces 60, either in the detection system 10 or the main system 20, so that the visualization system 40 may provide more accurate visualization of monitoring and detection and better situational awareness to the user. Such physical information may include, but is not limited to, a floorplan, map, and background, which may be in two dimensional or three dimensional. It will be appreciated that other information about a monitored space may be employed.

The processor 21 is also configured to communicate the processed information with the visualization system 40. The visualization system 40 includes a display interface 41. The display interface 41 is configured to provide the processed information related to the monitored space 60. The display interface 41 may be a web-based interface accessible by the user, or a display terminal, e.g., mounted on a wall. In some implementations, there may be more than one display interface 41. In some implementations, when the user stores physical information about a monitored space 60, the display interface 41 may provide the processed information along with the physical information about the monitored space 60 and may provide more accurate visualization of monitoring and detection and better situational awareness to the user.

The main system 20 may include an alert system 50, and the processor 21 may be configured to communicate the processed information with the alert system 50. The alert system 50 may be configured to notify the user of the system 1 of detected unwanted behaviors and/or undesirable conditions in the space 60, e.g., by alerting the user to distress and danger in the space 60, and allow the user to take action to address, mitigate, or remove the detected unwanted behaviors and/or undesirable conditions. In some implementations, when the detection system 10 detects unwanted behaviors and/or undesirable conditions in the space 60 in accordance with the rules the user set or a default setting, the system 1 may send out such detection to the user. Such rules the user set or a default setting may include detection of a loiterer, a high number of occupants, an emergency keyword, yelling and screaming, glass breaking, a gunshot, vaping, smoking, and a breach of a threshold, e.g., a temperature threshold, a formaldehyde level threshold, or a noise level (dB) threshold, in the space 60. It will be appreciated that other detection may be included. The alert system 50 may provide such detection to the user of the system 1 by electronic transmission, such as a text message, a mobile application push notification, an email, and combinations thereof. It will be appreciated that other methods of electronic transmission may be employed. In some implementations, the alert system 50 may communicate such detection with other communication systems of the user, e.g., a radio system, and trigger the other communications systems, e.g., the radio system, to alert security personnel to such detection, e.g., by playing an automated message over the radio system such as "Loitering detected in bathroom number 4" or "Vaping detected in classroom number 1." As such, by the alert system 50, the user of the system 1 may be promptly alerted to distress, danger, or other unwanted behaviors and/or undesirable conditions in the space 60 and be able to respond quickly, e.g., dispatching security personnel to the monitored space 60. In some implementations, the alert system 50 may be configured to send an alert to the user when certain conditions are met as set by the user or a default setting. For example, the user may configure the setting to receive an alert about a high number of occupants in the monitored space 60 only when the number of occupants 80 exceeds a high number threshold and persists in the space 60 more than a certain period time, e.g., 30 seconds. The user may also configure the setting to receive an alert only during a certain time period, e.g., operating hours, such as from 7 AM to 6 PM, or on certain dates, e.g., operating days, such as Monday through Friday, or both. It will be appreciated that other methods may be employed in configuring settings to receive an alert.

Figure 2A:
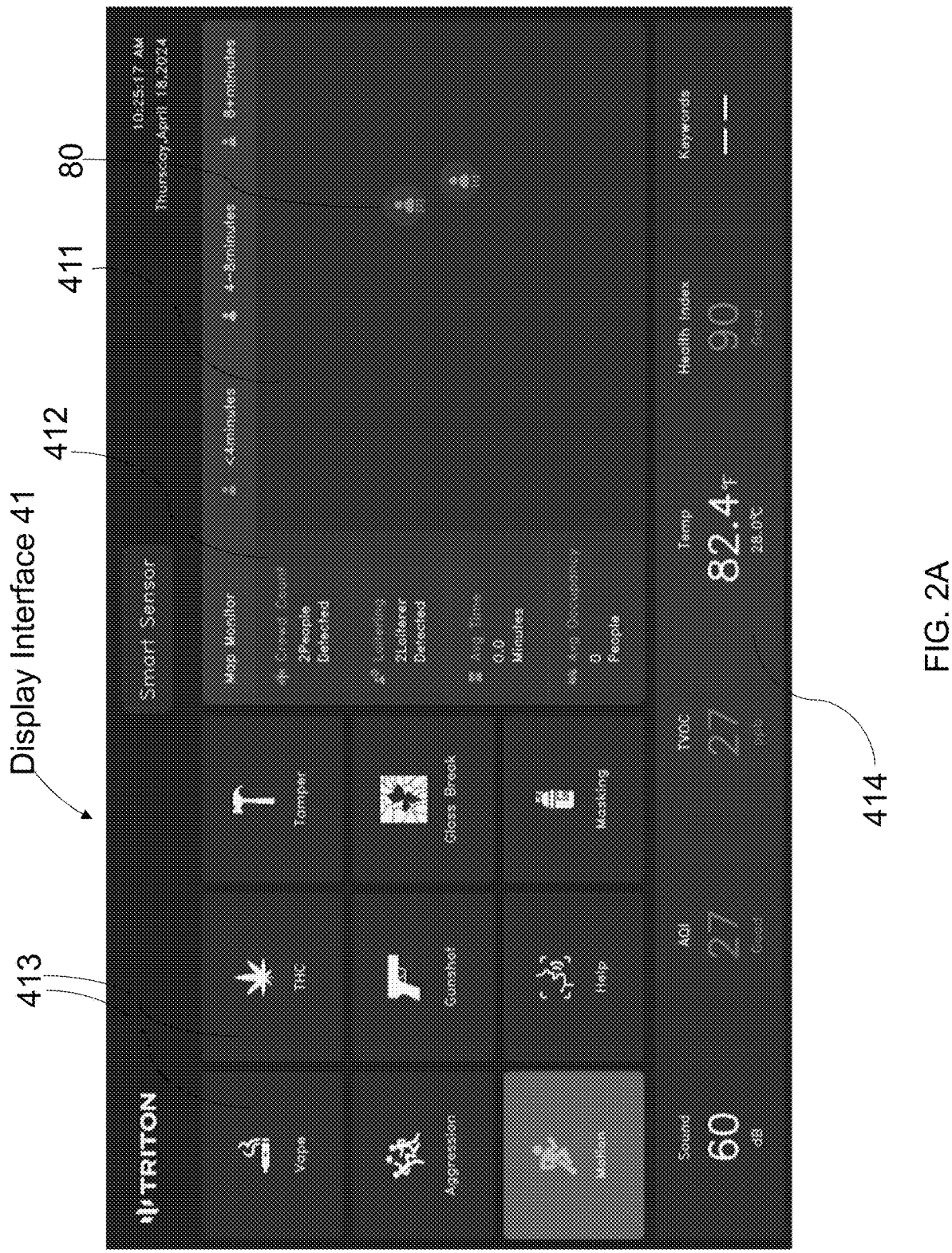
FIGS. 2A and 2B show schematic representations of a display interface of FIG. 1 displaying health and safety information, according to an example embodiment of the present disclosure.
Figure 2B:
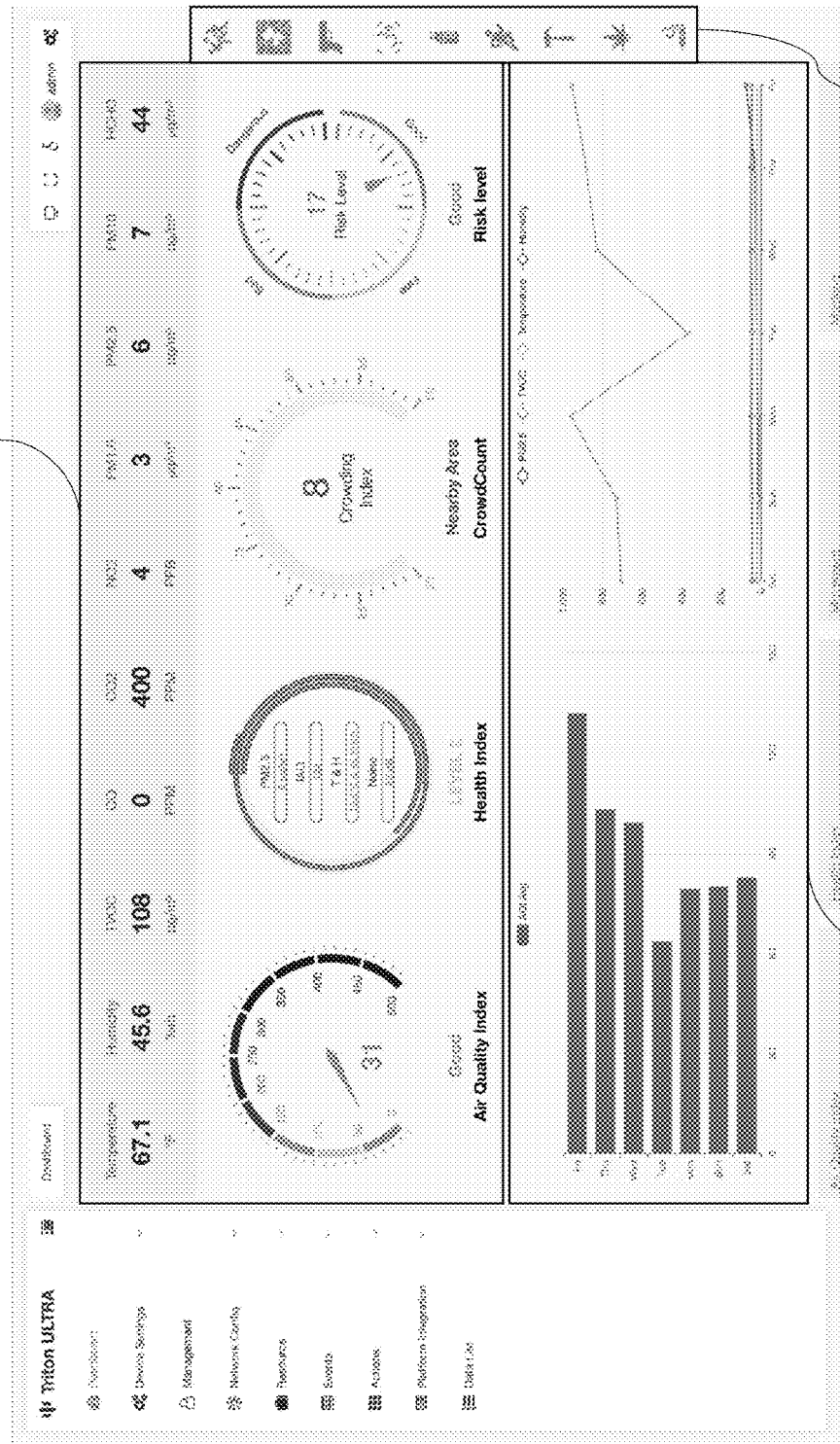

Referring to FIG. 2A, the display interface 41 is configured to represent health and safety information detected by the detection system 10 related to the monitored space 60. In some implementations, the detected information may include the presence of an occupant 80 in the space 60, and the display interface 41 may represent their relative locations in the space 60 on a portion 411. In some implementations, the display interface 41 may represent a total number of occupants 80 (crowding information) detected in the space 60 on the portion 411 or, separately, on another portion 412. In some implementations, on the portion 412, a number of people detected in the space (Crowd Count), a number of identified loiterers in the space (Loitering), an average occupancy time (Avg Time), and an average number of occupants in a certain time range as set by the user or a default setting, e.g., one minute, five minutes (AVG Occupancy) may be displayed. In some implementations, on a portion 413, detection of vaping (Vape), tetrahydrocannabinol (THC), tampering sounds (Tamper), aggression sounds (Aggression), gunshots (Gunshot), glass breaking sounds (Glass Break), motion (Motion), emergency keywords (Help), and masking (Masking) in the space 60 may be displayed. In some implementations, on a portion 414, the intensity of sounds in the space 60 measured in dB (Sound), an air quality index of the space 60 (AQI), measurement of total volatile organic compounds in the space 60 (TVOC), the temperature in the space 60 (Temp), a calculated health index (Health Index), and detection of keywords in the space 60 (Keywords) may be displayed. It will be appreciated that different methods may be employed to represent the detected information. In some implementations, the detection system 10 may be configured to detect tampering with the detection system 10. Such detection may include, but is not limited to, removing or carrying the detection system 10 to another location, or other movements of the detection system 10. The detection system 10 may include a 3-axis accelerometer and detect tampering attempts by determining the orientation of the detection system 10. When the orientation of the detection system 10 is not stable for a certain period of time, e.g., three seconds, the detection system 10 may determine and detect tampering attempts, and the Tamper sign may be activated on the portion 413 on the display interface 41. Referring to FIG. 2B, in some implementations, on a portion 414, the temperature, humidity, TVOC, carbon monoxide (CO), carbon dioxide (CO2), nitrogen dioxide (NO2), particulate matter (PM) categorized by size, such as PM 1.0, PM 2.5, and PM 10, and formaldehyde (HCHO) in the monitored space 60 may be represented in a number. An AQI, a calculated health index (Health Index), a calculated crowding information based on Crowd Count (Crowding Index), and a calculated risk level (Risk Level) may be represented in a color combined with a visual representation, such as a dial chart. In some implementations, Crowding Index may correspond to Crowd Count, and Crowding Index 8 denotes Crowd Count 8, conveying that there are eight detected people in the space 60 in visual representation, such as a dial chart. There may be a minimum number, e.g., 20, and/or maximum number, e.g., 60, of Crowd Count to be represented in Crowding Index, as configured by the user of the system 1. A default setting may be 0 for the minimum number and 100 for the maximum number. It will be appreciated that different methods may be employed to represent the detected health and safety information. In some implementations, on a portion 415, health and safety information may be represented on a weekly basis, e.g., for the last seven days. For example, on portion 415 of the display interface 41, the average AQI of each of the last seven days may be displayed so that the user of the system 1 may recognize trends or patterns of the air quality in the monitored space 60. In another example, on a different portion 415, PM 2.5, TVOC, temperature, and humidity for the last seven days in the monitored space 60 may be displayed in different colors so that the user of the system 1 may appreciate past trends or patterns of such information in the monitored space 60. It will be appreciated that different time periods and methods may be employed to represent the detected health and safety information.

In other implementations, the system 1 may monitor the presence of an occupant 80 in the space 60 and assign a unique identifier, e.g., a number, to the detected occupant 80, and the display interface 41 may represent the relative locations of the identified occupant 80 in the space 60 with the assigned unique identifier (e.g., [1] and [7] on the portion 411). The display interface 41 may further provide information as to the duration of each identified occupant 80 remaining in the space 60.

Figure 3:
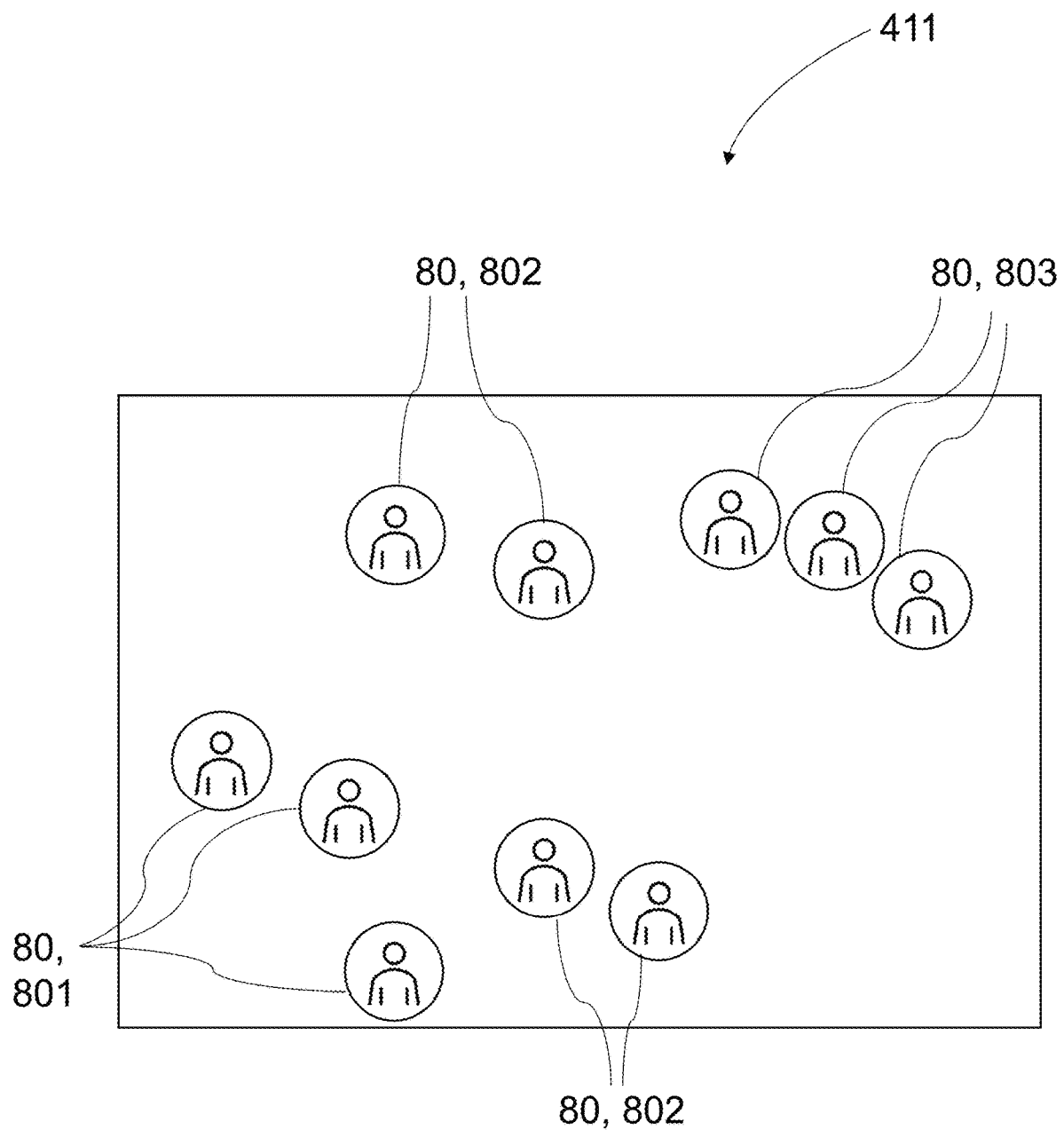
FIG. 3 shows a schematic representation of a portion of the display interface of FIG. 2A showing exemplary loitering information, according to an example embodiment of the present disclosure.

Referring to FIGS. 2A and 3, in some implementations, the duration of each identified occupant 80 can be associated with a unique identifier and may be represented by a color-code, for example, a green color 801 indicating the duration less than four minutes, an orange color 802 indicating the duration from four minutes to eight minutes, and a red color 803 indicating the duration of more than eight minutes. In other implementations, the unique identifier can be a number, a symbol, and/or a shape. It will be appreciated that different colors, criteria, and methods may be employed to represent the duration information. In some implementations, the user of the system 1 may consider a certain duration of remaining in the space 60 as a threshold of loitering and configure the system 1 to monitor and detect such loitering and the display interface 41 to represent the loitering information. The system 1 may monitor occupants and track their locations in the space 60 and the duration of time remaining in the space 60. The system 1 may track each identified occupant 80 in the space 60 in real-time and represent loitering information about the space 60 in real-time. For example, the user may set eight minutes as a threshold for loitering, and if there is an identified occupant remaining in the space 60 more than eight minutes, the system 1 may consider such an identified occupant as a loiterer, and the display interface 41 may represent the identified occupant with a color, e.g., red, and the relative location in the space 60. In this case, the system 1 may further dispatch security personnel to the space 60 to investigate or monitor such loitering to ensure safety and health in their establishment 70. The user may set four minutes as a threshold for high risk of loitering, and if there is an identified occupant remaining in the space 60 more than four minutes but not exceeding eight minutes, the system 1 may consider such an identified occupant as a high-risk occupant, but not a loiterer, and the display interface 41 may represent such an identified occupant with a different color, e.g., orange, and their relative location in the space 60. In this case, the system 1 may further dispatch security personnel to the space 60 to investigate or keep tracking such a high risk-occupant whether they remain in the space 60 more than eight minutes. If such a high-risk occupant continues to remain in the space 60, and the duration time (the duration of time remaining in the space) in the space 60 exceeds eight minutes, now they are considered a loiterer, and the system may represent them with, e.g., a red color. If there is an identified occupant remaining in the space 60 less than four minutes, they may not be considered as neither a loiterer nor a high-risk occupant and may be represented in a different color, e.g., green, but may be counted in the total number of occupants 80 (crowding information). It will be appreciated that other methods and thresholds may be employed in determining loitering, and other metrics, such as the movement of an occupant (e.g., remaining idle), may be factored into determining loitering. In some implementations, the detection system 10 may further include an alarm module 16, e.g., a speaker, and the user of the system 1 may set rules to alarm, e.g., by playing an automated message through the speaker 16, when the system 1 detects a loiterer or a high-risk occupant, in accordance with the rules set by the user, in the monitored space 60. Such an automated message may include, e.g., "Loitering detected." In an educational environment, an automated message may include, e.g., "Loitering detected. Get to class" or "Loitering detected in bathroom #4", etc. In this case, the volume of an automated message may be adjusted by the detection system 10 or the main system 20, or both. It will be appreciated that other methods may be employed.

Figure 4:
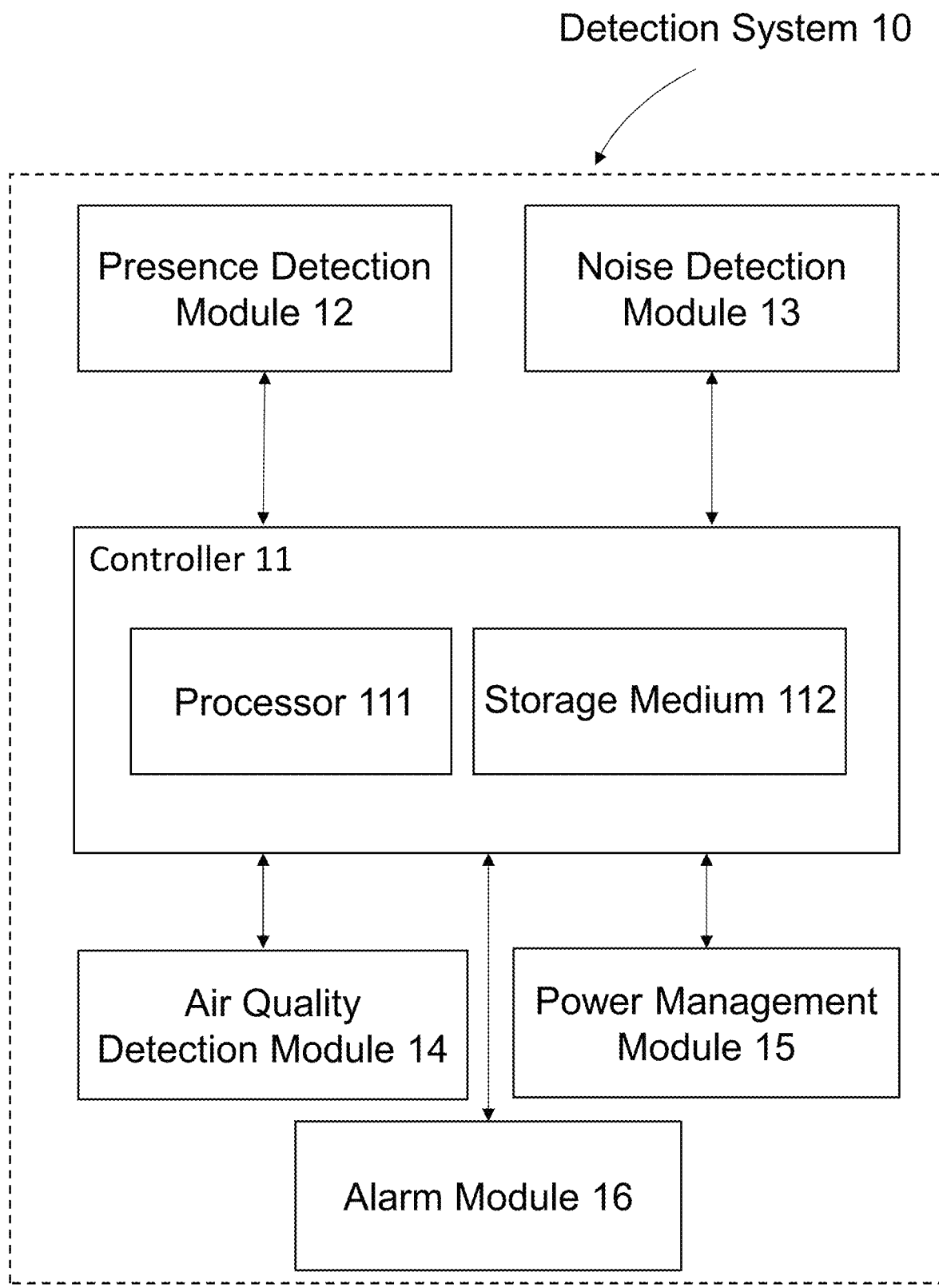
FIG. 4 shows a schematic representation of a detection system of the system of FIG. 1, according to an example embodiment of the present disclosure.

Referring to FIG. 4, the detection system 10 includes a controller 11 and a presence detection module 12 configured to monitor, track, or count occupants 80 in a way that respects individuals' rights to privacy within a monitored space 60, and the system 1 is configured to provide occupancy information, including, but not limited to, loitering information, crowding information, line crossing detection, and flow counting. Such occupancy information may include (i) a number of occupants 80 in the monitored space 60; (ii) a duration time of each occupant 80 remaining in the monitored space 60; (iii) a location of each occupant 80 being located in the monitored space 60; (iv) entrance of an occupant 80 into the monitored space 60; (v) a departure of an occupant 80 from the monitored space 60; (vi) a number of occupants 80 entered into the monitored space 60; (vii) a number of occupants 80 exiting the monitored space 60; and (viii) an average number of occupants 80 in the monitored space 60 in a certain time range as set by the user or a default setting e.g., one minute, three minutes. In some implementations, the user of the system 1 may store physical information about monitored spaces in the detection system 10 so that the detection system 10 may provide more accurate visualization of monitoring and detection and better situational awareness to the user. Such physical information may include, but is not limited to, a floorplan, map, and background, which may be in two dimensional or three dimensional. It will be appreciated that other information about a monitored space may be employed. As such, a user of the system 1 will be able to monitor the space 60 and ensure the safety and health in their establishment effectively and accurately. The detection system 10 may include other modules, such as, a noise detection module 13, an air quality detection module 14, a power management module 15, and an alarm module 16 for monitoring the space 60. The controller 11 may include a processor 111 and a storage medium 112. The processor 111 may receive signals from modules 12, 13, 14, 15 and process the signals via execution of instructions. The storage medium 112 may include a readable and writable storage medium communicatively coupled to the processor 111 and storing instructions that are executable by the processor 111. The storage medium 112, which stores a database, may comprise any storage media, or group of storage media, readable by the processor 111, and capable of storing software and data. The storage medium 112 can include volatile and non-volatile, removable and non-removable media implemented in any method or technology for storage of information, such as computer-readable instructions, data structures, program modules, or other data. The storage medium 112 may be implemented as a single storage device but may also be implemented across multiple storage devices or subsystems located at disparate locations and communicatively connected, such as in a cloud computing system. Examples of storage media include random access memory, read only memory, optical discs, flash memory, virtual memory, and non-virtual memory, or any other medium which can be used to store the desired information and may be accessed by processor 111.

The detection system 10 may transmit processed signals to the main system 20. In some implementations, the controller 11 may function as a controller for modules, individually or in concert with the controller for the modules, and thus may be configured to support and control the modules 12, 13, 14, 15, 16.

Figure 5:
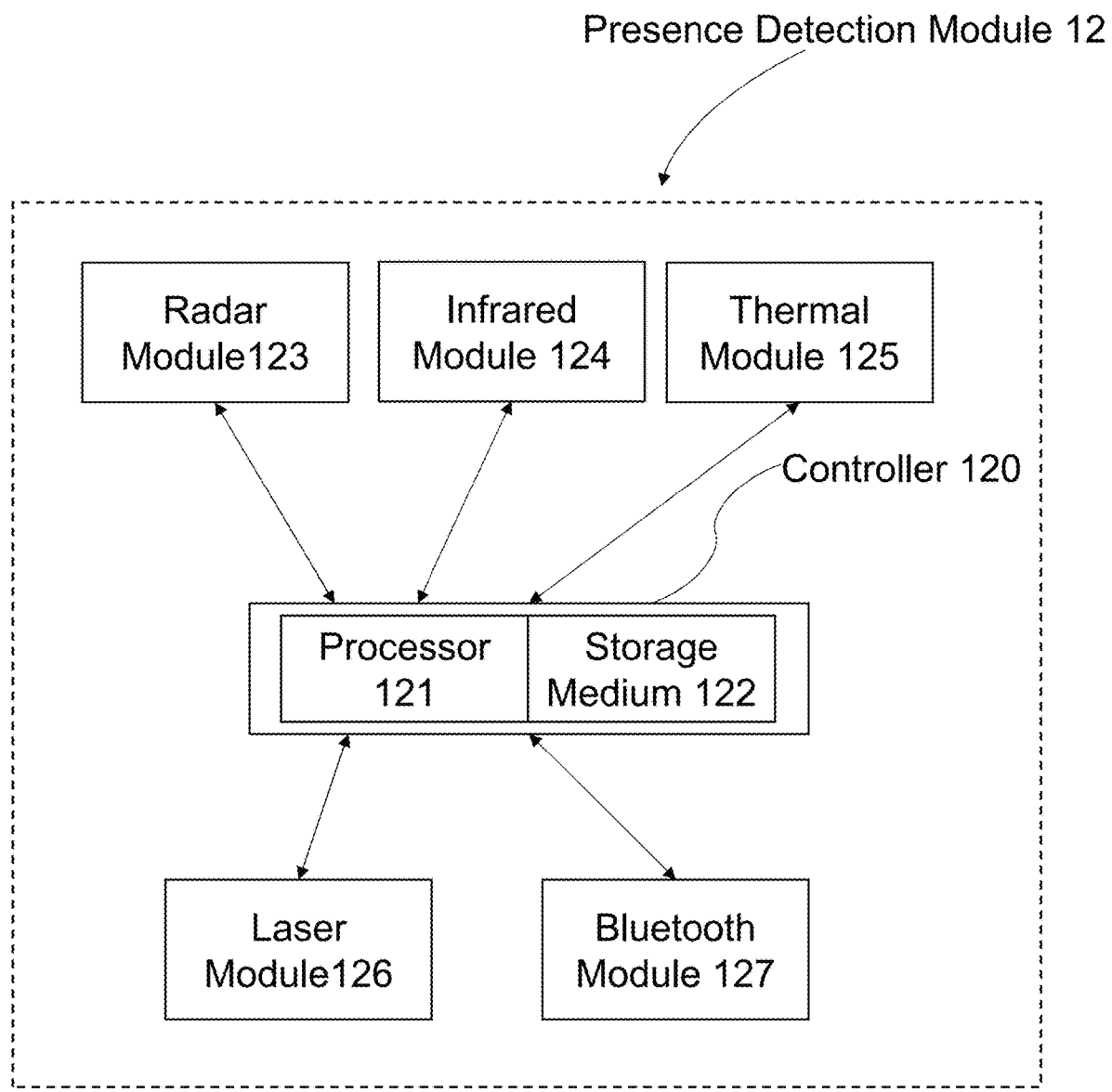
FIG. 5 shows a schematic representation of a presence detection module of the detection system of FIG. 4, according to an example embodiment of the present disclosure.

Referring to FIG. 5, the presence detection module 12 includes a controller 120 and one or more modules for presence and/or location detection. Modules for presence detection may include a radar module 123, an infrared module 124, a thermal module 125, a laser module 126, and a Bluetooth module 127, or combinations thereof. It will be appreciated that any other suitable modules for presence detection may be employed. The controller 120 may include a processor 121 and a storage medium 122. The processor 121 may receive signals from modules 123, 124, 125, 126, 127 and process the signals via execution of instructions. The storage medium 122 may include a readable and writable storage medium communicatively coupled to the processor 121 and storing instructions that are executable by the processor 121. In some implementations, the controller 120 may function as a controller for modules, individually or in concert with the controller for the modules, and thus may be configured to support and control the modules 123, 124, 125, 126, 127.

Figure 6:
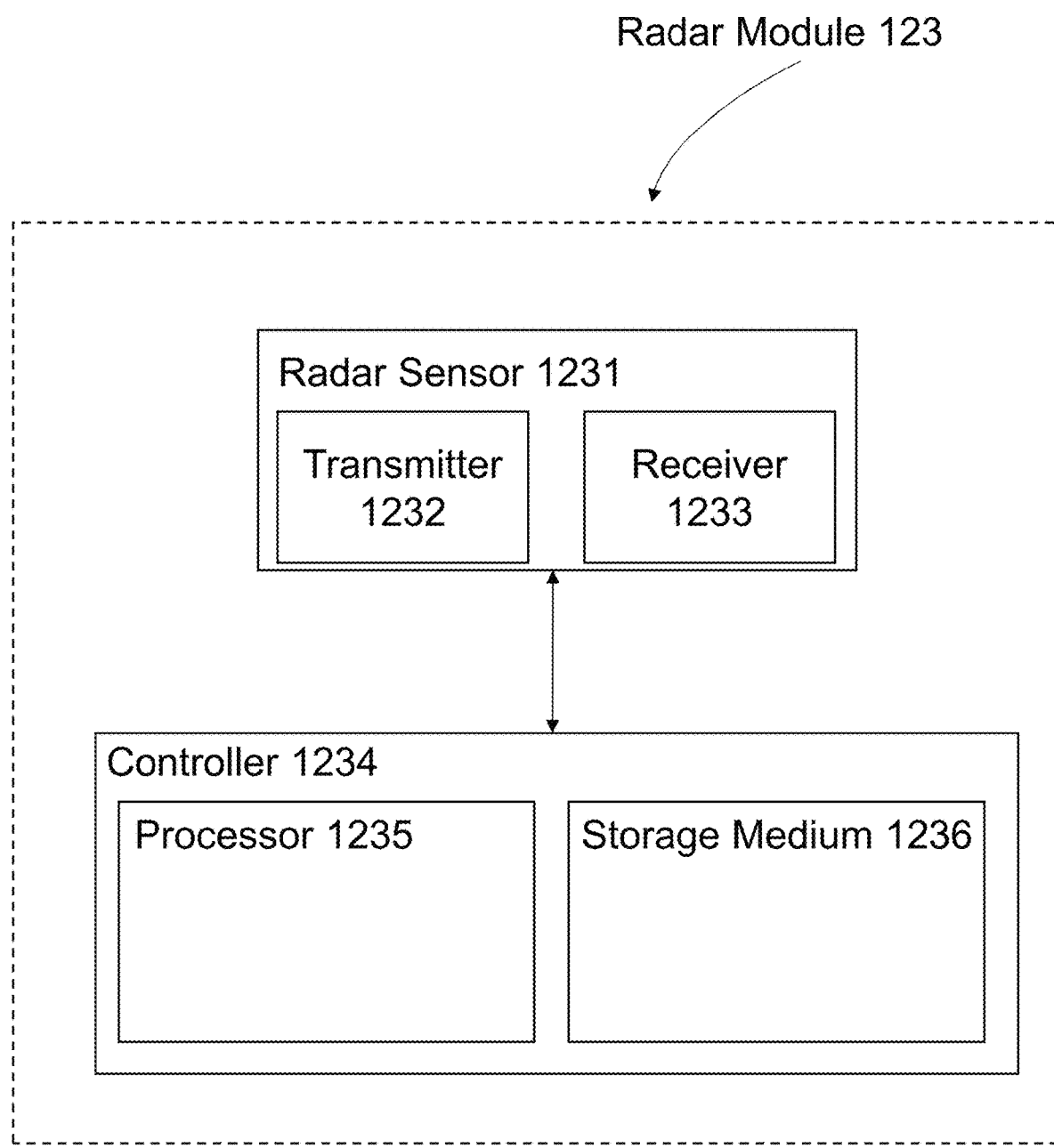
FIG. 6 shows a schematic representation of a radar module of the presence detection module of FIG. 5, according to an example embodiment of the present disclosure.

Referring to FIGS. 5 and 6, in some implementations, the presence detection module 12 may include a radar module 123. The radar module 123 may include a radar sensor 1231 configured to emit signals, i.e., radio waves, and detect reflections of the emitted signals from multiple objects, and a controller 1234 configured to analyze the detected reflections and determine the presence and movement of occupants 80. The radar sensor 1231 may include a transmitter 1232 configured to emit signals and a receiver 1233 configured to receive and detect reflections. The controller 1234 may include a processor 1235 and a storage medium 1236. The processor 1235 may receive signals from the radar sensor 1231 and process the signals via execution of instructions. The storage medium 1236 may include a readable and writable storage medium communicatively coupled to the processor 1235 and storing instructions that are executable by the processor 1235. In some implementations, the controller 120 may function as a controller for the radar module 123, individually or in concert with the controller 1234, and thus be configured to support and control the radar module 123. In some implementations, the radar module 123 may be configured to use millimeter wave signals, for example. In some implementations, the radar module 123 may employ the time-of-flight (ToF) method and calculate the time taken for each signal to travel to an object and back. The processor 1235 may determine the presence and movement of occupants 80 within a monitored space 60 simultaneously. The radar module 123 may provide real-time counting or tracking, or both, of occupants 80 in the monitored space 60. In some implementations, the radar module 123 may be configured to detect human vital signs, such as heartbeat and respiration. For example, the radar module 123 can measure the movements of the chest of the occupants 80 during respiration by emitting radio waves in the form of electromagnetic radiation. It will be appreciated that other components and methods may be employed to detect human presence or track human movement, or both. In some implementations, the radar module 123 may be configured to for a line crossing approach. Specifically, the user of the system 1 may set a certain space 60 in their establishment 70 as a restricted area, and the radar module 123 may detect entrance of an occupant 80 into the monitored space 60 by detecting human presence in the monitored space 60. The user of the system 1 may also configure the radar module 123 to track the movement of an occupant 80, e.g., with a unique identifier, and detect the departure of the occupant 80 from the monitored space 60. For example, in a hospital setting, the radar module 123 may be configured to track and monitor whether a patient leaves his/her bed. In other settings, the radar module 123 can make sure people do not access restricted area(s) and send an alert to the system 1. It will be appreciated that other methods may be employed in the line counting approach. In other implementations, the radar module 123 may be configured for a flow counting approach. Specifically, the radar module 123 may be configured for flow counting by tracking a number of occupants 80 entering into the monitored space 60 and/or a number of occupants 80 exiting the monitored space 60 and counting the numbers. It may be a total number of occupants entered into the monitored space 60, or a number of occupants 80 entering/exiting the monitored space 60 in a certain time range as set by the user or a default setting, e.g., per minute or every three minutes. The radar module 123 may also be configured to track and count an average number of occupants 80 in the monitored space 60 in a certain time range as set by the user or a default setting. It will be appreciated that other methods may be employed in the flow counting approach.

Figure 7:
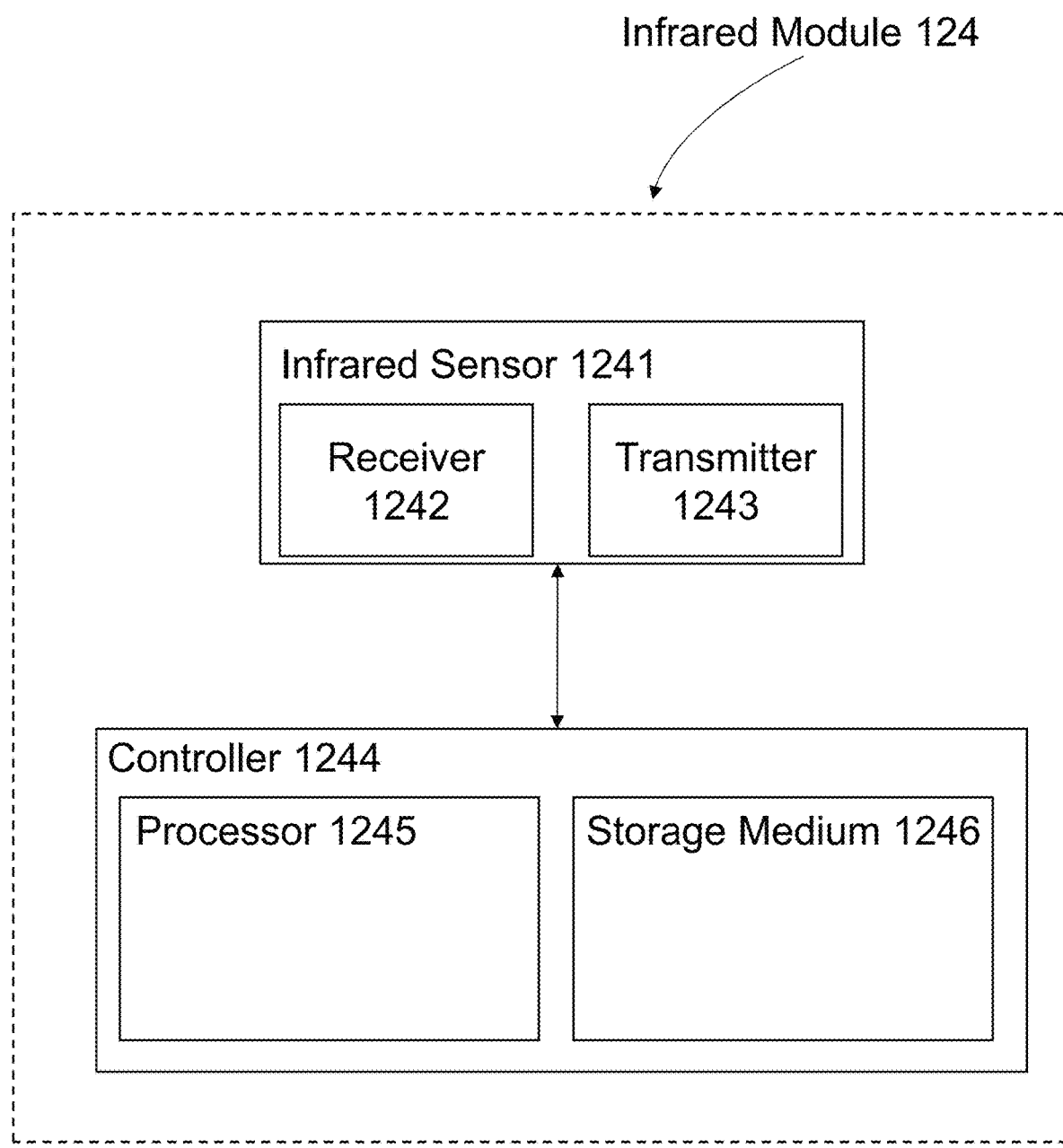
FIG. 7 shows a schematic representation of an infrared module of the presence detection module of FIG. 5, according to an example embodiment of the present disclosure.

Referring to FIGS. 5 and 7, in some implementations, the presence detection module 12 may include an infrared module 124. The infrared module 124 may include an infrared sensor 1241 configured to detect infrared radiation emitted by human bodies and a controller 1244 configured to analyze the detected radiation and determine the presence and movement of occupants 80. The infrared sensor 1241 may include a receiver 1242 and may be configured as an active infrared sensor (including a transmitter 1243) or a passive infrared sensor (without a transmitter 1243). The controller 1244 may include a processor 1245 and a storage medium 1246. The processor 1245 may receive signals from the infrared sensor 1241 and process the signals via execution of instructions. The storage medium 1246 may include a readable and writable storage medium communicatively coupled to the processor 1245 and storing instructions that are executable by the processor 1245. In some implementations, the controller 120 may function as a controller for the infrared module 124, individually or in concert with the controller 1244, and thus be configured to support and control the infrared module 124. In some implementations, the infrared module 124 may employ the time-of-flight (ToF) method and calculate the time taken for each signal to travel to an object and back. The infrared module 124 may provide real-time counting or tracking, or both, of occupants 80 within a monitored space 60. In some implementations, the infrared module 124 may receive and detect infrared radiation emitted by warm objects, such as humans, and detect movement by measuring changes in infrared radiation emitted by the human body. Yet, in some implementations, the infrared module 124 may transmit infrared light and detect human presence and/or movement by receiving and analyzing the reflection of the infrared light or by detecting the interruption of the infrared light. It will be appreciated that other components and methods may be employed to detect human presence or track human movement, or both. In some implementations, the infrared module 124 may be configured to for a line crossing approach. Specifically, the user of the system 1 may set a certain space 60 in their establishment 70 as a restricted area, and the infrared module 124 may detect entrance of an occupant 80 into the monitored space 60 by detecting human presence in the monitored space 60. The user of the system 1 may also configure the infrared module 124 to track the movement of an occupant 80, e.g., with a unique identifier, and detect the departure of the occupant 80 from the monitored space 60. For example, in a hospital setting, the infrared module 124 may be configured to track and monitor whether a patient leaves his/her bed. It will be appreciated that other methods may be employed in the line counting approach. In other implementations, the infrared module 124 may be configured for a flow counting approach. Specifically, the infrared module 124 may be configured for flow counting by tracking a number of occupants 80 entering into the monitored space 60 and/or a number of occupants 80 exiting the monitored space 60 and counting the numbers. It may be a total number of occupants entered into the monitored space 60, or a number of occupants 80 entering/exiting the monitored space 60 in a certain time range as set by the user or a default setting, e.g., per minute or every three minutes. The infrared module 124 may also be configured to track and count an average number of occupants 80 in the monitored space 60 in a certain time range as set by the user or a default setting. It will be appreciated that other methods may be employed in the flow counting approach.

Figure 8:
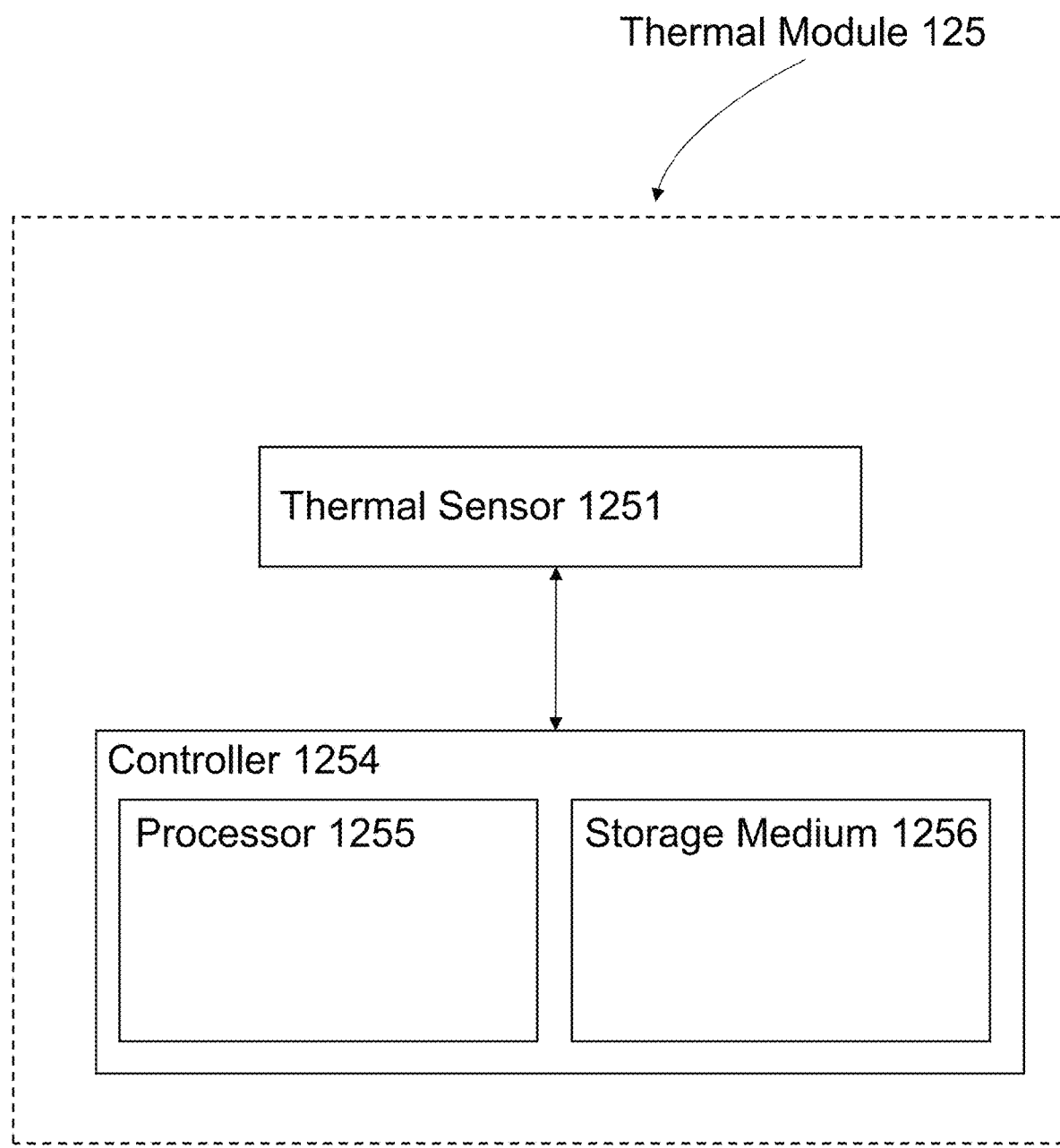
FIG. 8 shows a schematic representation of a thermal module of the presence detection module of FIG. 5, according to an example embodiment of the present disclosure.

Referring to FIGS. 5 and 8, in some implementations, the presence detection module 12 may include a thermal module 125. The thermal module 125 may include a thermal sensor 1251, e.g., a thermal imager or thermal imaging camera, configured to detect signals, i.e., heat, emitted by objects and a controller 1254 configured to analyze the detected heat and temperature variations caused by human presence and determine the presence and movement of occupants 80. The controller 1254 may include a processor 1255 and a storage medium 1256. The processor 1255 may receive signals from the thermal sensor 1251 and process the signals via execution of instructions. In some implementations, the thermal sensor 1251 may identify an occupant as a blob, a distinct region in a thermal image, and may have a resolution that is high enough to identify the occupant. It will be appreciated that any other suitable resolution may be employed in identifying occupants, and more than one thermal sensor may be employed. The storage medium 1256 may include a readable and writable storage medium communicatively coupled to the processor 1255 and storing instructions that are executable by the processor 1255. In some implementations, the controller 120 may function as a controller for the thermal module 125, individually or in concert with the controller 1254, and thus be configured to support and control the thermal module 125. The thermal module 125 may provide real-time counting or tracking, or both, of occupants 80 within a monitored space 60. In some implementations, a thermal sensor 1251 may detect heat emitted from occupants in the space 60 and analyze characteristic heat signatures. The thermal sensor 1251 may also track movement and identify occupants 80 based on their thermal profiles. It will be appreciated that other components and methods may be employed to detect human presence or track human movement, or both. In some implementations, the thermal module 125 may be configured for a line crossing method. Specifically, the user of the system 1 may set a certain space 60 in their establishment 70 as a restricted area, and the thermal module 125 may detect entrance of an occupant 80 into the monitored space 60 by detecting human presence in the monitored space 60. The user of the system 1 may also configure the thermal module 125 to track the movement of an occupant 80, e.g., with a unique identifier, and detect the departure of the occupant 80 from the monitored space 60. For example, in a hospital setting, the thermal module 125 may be configured to track and monitor whether a patient leaves his/her bed. In some implementations, the thermal module 125 may be configured for flow counting. It will be appreciated that other methods may be employed in the line counting method. In other implementations, the thermal module 125 may be configured for a flow counting method by tracking a number of occupants 80 entering into the monitored space 60 and/or a number of occupants 80 exiting the monitored space 60 and counting the numbers. It may be a total number of occupants entered into the monitored space 60, or a number of occupants 80 entering/exiting the monitored space 60 in a certain time range as set by the user or a default setting, e.g., per minute or every three minutes. The thermal module 125 may also be configured to track and count an average number of occupants 80 in the monitored space 60 in a certain time range as set by the user or a default setting. It will be appreciated that other methods may be employed in the flow counting method. In other implementations, the thermal module 125 is configured to detect an elevated heat of an object or room temperature, indicating a possible fire condition. The alert system 50 may then send out such detection to the user so that the user can respond to and control it.

Figure 9:
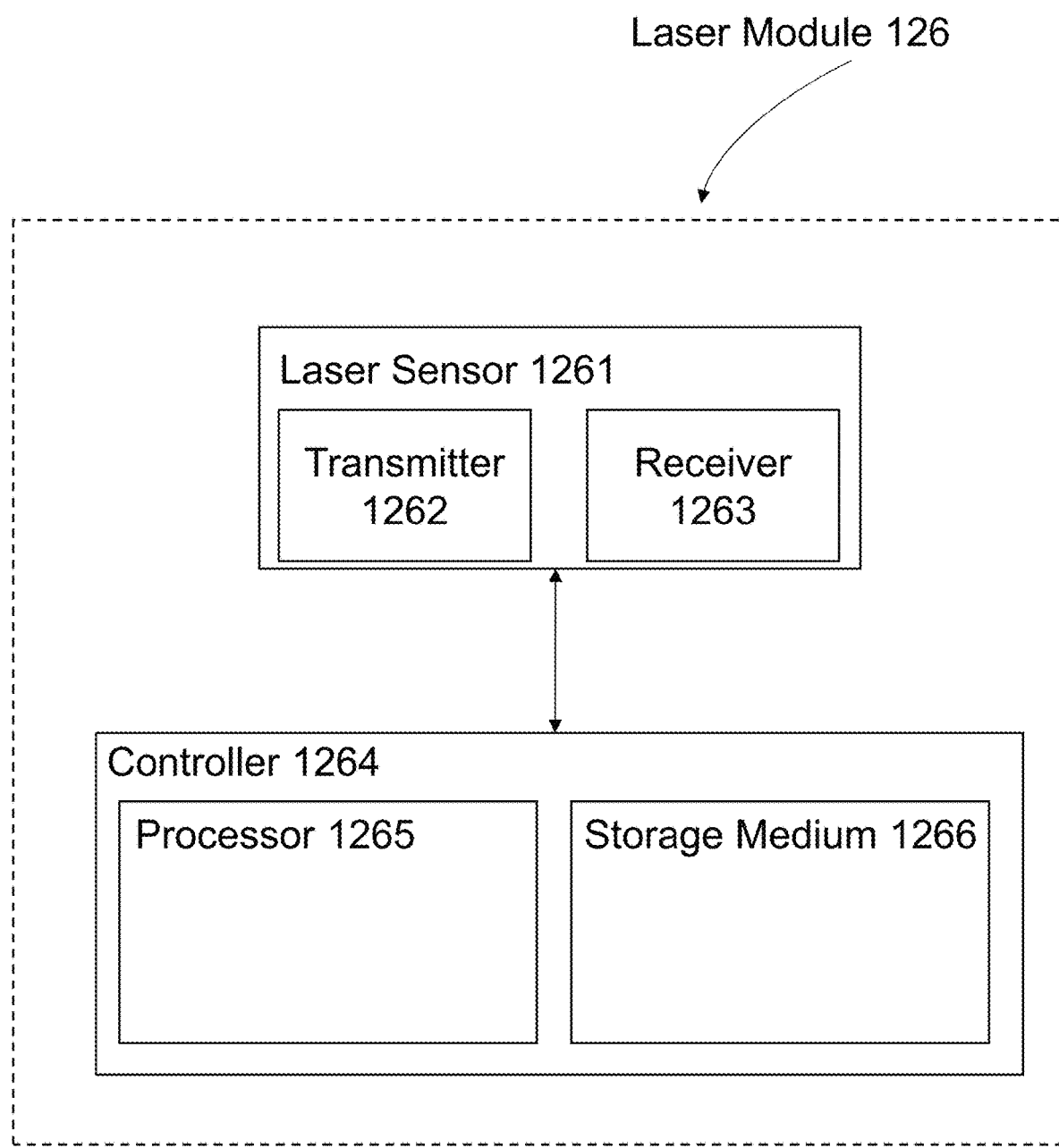
FIG. 9 shows a schematic representation of a laser module of the presence detection module of FIG. 5, according to an example embodiment of the present disclosure.

Referring to FIGS. 5 and 9, in some implementations, the presence detection module 12 may include a laser module 126. The laser module 126 may include a laser sensor 1261 configured to produce laser signals and receive reflected laser signals and a controller 1264 configured to process the received signals to detect human presence and movement. The laser sensor 1261 may include a laser transmitter 1262 to produce laser signals and a receiver 1263 to receive reflected laser signals. The controller 1264 may include a processor 1265 and a storage medium 1266. The processor 1265 may receive signals from the laser sensor 1261 and process the signals via execution of instructions. The storage medium 1266 may include a readable and writable storage medium communicatively coupled to the processor 1265 and storing instructions that are executable by the processor 1265. In some implementations, the controller 120 may function as a controller for the laser module 126, individually or in concert with the controller 1264, and thus be configured to support and control the laser module 126. The laser module 126 may provide real-time counting or tracking, or both, of occupants 80 within a monitored space 60. The laser module 126 may emit a continuous laser beam towards the monitored space 60 and measure the time it takes for the laser beam to travel to objects and back, the angle of the reflected beam, or the change in frequency of the reflected laser beam, or combinations thereof. The laser module 126 may analyze and determine the presence of a human or occupants and their movement in the space 60. In some implementations, the laser module 126 may employ light detection and ranging or laser imaging, detection, and ranging (LiDAR) technology. The laser sensor 1261 may emit pulses of laser light by the transmitter 1262 and receive reflected laser pulses by the receiver 1263. Each laser pulse travels to an object in the monitored space 60. The laser module 126 may employ the time-of-flight (ToF) method and calculate the time taken for each pulse to travel to an object and back. Thus, the laser module 126 may analyze and determine the presence of a human or occupants and their movement in the space 60. It will be appreciated that other components and methods may be employed to detect human presence or track human movement, or both. In some implementations, the laser module 126 may be configured for a line crossing method. The user of the system 1 may set a certain space 60 in their establishment 70 as a restricted area, and the laser module 126 may detect entrance of an occupant 80 into the monitored space 60 by detecting human presence in the monitored space 60. The user of the system 1 may also configure the laser module 126 to track the movement of an occupant 80, e.g., with a unique identifier, and detect the departure of the occupant 80 from the monitored space 60. For example, in a hospital setting, it may be configured to track and monitor whether a patient leaves his/her bed. It will be appreciated that other methods may be employed in the line counting method. In some implementations, the laser module 126 may be configured for a flow counting method. Specifically, the laser module 126 may be configured for flow counting by tracking a number of occupants 80 entering into the monitored space 60 and/or a number of occupants 80 exiting the monitored space 60 and counting the numbers. It may be a total number of occupants entered into the monitored space 60, or a number of occupants 80 entering/exiting the monitored space 60 in a certain time range as set by the user or a default setting, e.g., per minute or every three minutes. The laser module 126 may also be configured to track and count an average number of occupants 80 in the monitored space 60 in a certain time range as set by the user or a default setting. It will be appreciated that other methods may be employed in the flow counting method.

Figure 10:
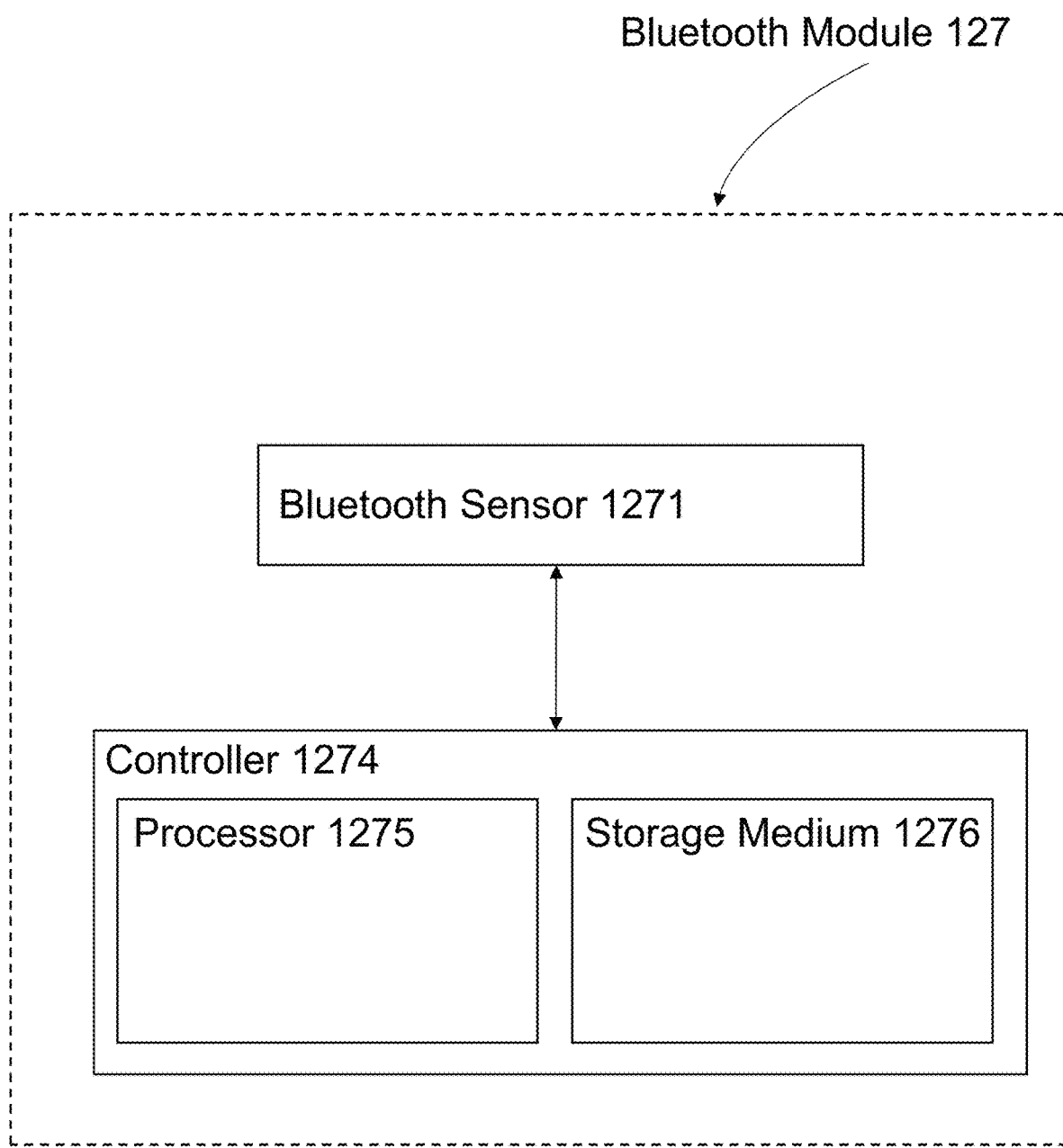
FIG. 10 shows a schematic representation of a Bluetooth module of the presence detection module of FIG. 5, according to an example embodiment of the present disclosure.

Referring to FIGS. 5 and 10, in some implementations, the presence detection module 12 may include a Bluetooth module 127. The Bluetooth module 127 may include a Bluetooth sensor 1271 configured to detect Bluetooth signals, including Bluetooth Low Energy (BLE) signals, from mobile devices and a controller 1274 configured to analyze the detected Bluetooth signals and determine the number of mobile devices within the monitored space 60. The controller 1274 may include a processor 1275 and a storage medium 1276. The processor 1275 may receive signals from the Bluetooth sensor 1271 and process the signals via execution of instructions. The storage medium 1276 may include a readable and writable storage medium communicatively coupled to the processor 1275 and storing instructions that are executable by the processor 1275. In some implementations, the controller 120 may function as a controller for the Bluetooth module 127, individually or in concert with the controller 1274, and thus be configured to support and control the Bluetooth module 127. The Bluetooth sensor may operate continuously, and the Bluetooth module 127 may provide real-time counting of occupants 80 within a monitored space 60. In many establishments, people visiting or using establishments are likely to carry a mobile device, including a smartphone, and nowadays, it is a common feature of mobile devices to have Bluetooth connections, and such mobile devices emit Bluetooth signals. In some implementations, the Bluetooth module 127 may detect such Bluetooth signals in the monitored space 60 and filter out Bluetooth signals emitted from mobile devices that are not smartphones. For example, a database containing characteristics of signals emitting from non-smartphones, e.g., smart watches, laptops, and home appliances, may be stored in the storage medium 1276, and the Bluetooth module 127 may exclude those detected devices corresponding to the database from counting. In some implementations, in excluding non-smartphone devices, e.g., smart watches, laptops, and home appliances, the Bluetooth module 127 may store their MAC (medium access control) addresses in a database stored in the storage medium 1276. Some of their MAC addresses may be retained temporarily to ensure privacy. By only tracking Bluetooth signals from smartphones, the Bluetooth module 127 may count the number of occupants in the space 60. Assuming that each occupant is carrying one smartphone, the Bluetooth module 127 may provide the number of occupants in the monitored space 60. In some implementations, the Bluetooth module 127 may measure the strength of received signals to exclude mobile devices not in the monitored space 60, e.g., emitting signals with weak strength. The Bluetooth module 127 may employ a received signal strength indicator (RSSI) value in defining a detection range, i.e., a distance, from the detection system 10 in the monitored space 60. A greater RSSI value means a stronger signal. Thus, when an RSSI value is represented in negative form, a value closer to 0 means a stronger signal. The Bluetooth module 127 may analyze RSSI values of signals and calculate the distance from each RSSI value and only count those mobile devices, i.e., smartphones, within a certain distance as set by the user or a default setting, e.g., three meters or five meters from the detection system 10, in providing crowding information. In some implementations, the Bluetooth module 127 may analyze transmit power (TX power) from Bluetooth devices and filter out Bluetooth devices with TX power lower than a threshold. TX power may be measured in decibels per milliwatt (dBm), and for example, Bluetooth devices with lower than 8 (dBm) TX power may be filtered out and not be counted toward the number of occupants in the monitored space 60. In some implementations, the Bluetooth module 127 may consider TX power of a Bluetooth device in defining a distance from the detection system 10 or adjust the distance estimated from RSSI values. In some implementations, the Bluetooth module 127 may filter out Bluetooth devices based on their manufacturers' BLE company identifier codes (CIC) and count only certain manufacturers' devices in counting the number of occupants in the monitored space 60. It will be appreciated that other components and methods may be employed. It will also be appreciated that any suitable Bluetooth technology and devices regardless of their versions and classes may be employed.

In some implementations, the presence detection model 12 may include a Bluetooth module 127 for Bluetooth device detection, including cell phone/smartphone detection. It may be beneficial in places where there are limits or restrictions on mobile device use or smartphone use, such as schools or secure facilities, including correctional facilities. For example, the Bluetooth module 127 may detect Bluetooth signals and count the number of Bluetooth devices in a monitored space. In some implementations, the Bluetooth module 127 may exclude Bluetooth devices other than smartphones and only track Bluetooth signals from smartphones. Thus, the Bluetooth module 127 may detect the use of smartphones in a space and count such use. In some implementations, Bluetooth devices may emit Bluetooth signals even when they are in a mode that suspends the device's radio-frequency (RF) signal transmission technologies, e.g., airplane mode. Then, the Bluetooth module 127 may still detect Bluetooth signals from smartphones in such mode and may provide information about whether and/or where smartphones are in a space. In other implementations, Bluetooth devices may emit Bluetooth signals even when they are turned/powered off. Then, the Bluetooth module 127 may also detect Bluetooth signals from such smartphones that are turned/powered off. In some implementations, the Bluetooth module 127 may filter out known Bluetooth devices from smartphone detection. For example, if there are smartphones that belong to security personnel or staff of a secure facility in a space, the Bluetooth module 127 may filter out these known Bluetooth devices in identifying and detecting smartphone use in the space. The Bluetooth module 127 may filter out these known devices individually.

The Bluetooth module 127 may also filter out these known Bluetooth devices by filtering out a list of Bluetooth device addresses, or Bluetooth MAC addresses, unique identifiers assigned to each Bluetooth device by their manufacturers. It will be appreciated that other suitable methods may be employed to filter out known devices. In some implementations, the Bluetooth module 127 may provide information about whether and/or where smartphone use is in the space by analyzing RSSI values and/or TX power and their relative locations in the space and may represent their locations on the display interface 41. The presence detection module may alert the user to cell phone/smartphone detection. It will be appreciated that any suitable algorithms and methods may be employed for cell/phone/smartphone detection. In some implementations, referring to FIG. 2A, the display interface 41 may be configured to represent smartphone detection with respect to the monitored space 60. The display interface 41 may represent smartphone detection and their relative locations in the space 60. It will be appreciated that other suitable methods may be employed to represent smartphone detection.

In some implementations, the presence detection module 12 may include a radar module 123 (FIG. 6), a thermal module 125 (FIG. 8), or both for fall detection. It may be beneficial in nursing facilities or healthcare facilities settings. For example, a thermal module 125 may trace an identified occupant in a space and compare the posture of an occupant in a space using a thermal sensor 1251 with postures in a database stored in a storage medium 1256, which includes various postures, including postures of standing positions, postures of lying positions, and postures of sleeping positions. Postures of different positions may have distinct features, and if an occupant falls, e.g., from a bed, the occupant's posture would correspond to or be similar to one of the postures of lying positions rather than the postures of standing positions or postures of sleeping positions. In some implementations, the main system 20 may include such a database in the storage medium 22 (FIG. 1), and the main system 20 may compare the detected postures with postures in the database in the storage medium 22. Yet, in some implementations, the presence detection module 12 may, in concert with the main system 20, compare the detected postures with those in the database stored in the storage medium 1256 and/or the database in the storage medium 22. The thermal sensor 1251 may identify an occupant as a blob and may have a resolution that is high enough to identify the posture of the identified occupant and low enough not to collect personally identifiable information. It will be appreciated that any other suitable resolution may be employed, and more than one thermal sensor may be employed. An algorithm may be employed to compare and identify fall postures, utilizing artificial intelligence (AI), including machine learning and/or deep learning. The database may also include thermal images of environments, e.g., walls, surrounding, including, beds and tables, and other objects, and the algorithm may filter them out in tracing occupants. When the algorithm finds a posture corresponding to, or matching, one of the fall postures in the database, the presence detection module 12 recognizes and detects a fall and alerts the user to fall detection. It will be appreciated that any suitable algorithms and methods may be employed for fall detection. In another example, a radar module 123 may trace an identified occupant in the space for fall detection. The radar module 123 may be configured to use millimeter wave signals, for example, with a frequency of 60 GHz or 80 GHZ, or therebetween, including 79 GHz, which can detect human vital signs, including micro-tremors. It will be appreciated that any other suitable frequencies may be employed. The radar module 123 may detect such microtremors, distinguish occupants from objects in the space, analyze occupants' breathing rates, and identify their breathing patterns, i.e., whether an identified occupant is sleeping, breathing normally, or breathing heavily. Such analysis may be employed for health diagnostics but also may be employed for fall detection. It will be appreciated that more than one radar modules 123 connected to each other may be employed for better accuracy. The radar module 123 may detect and recognize the breathing patterns of occupants and compare those patterns with breathing patterns in a database stored in a storage medium 1236 containing various breathing patterns, including sudden changes to breathing patterns in the case of a fall. In some implementations, the main system 20 may include such a database in the storage medium 22 (FIG. 1), and the main system 20 may compare the detected breathing patterns with breathing patterns in the database in the storage medium 22. Yet, in some implementations, the presence detection module 12 may, in concert with the main system 20, compare the detected breathing patterns with those in the database stored in the storage medium 1236 and/or the database in the storage medium 22. An algorithm may be employed to compare and identify breathing patterns, utilizing artificial intelligence (AI), including machine learning and/or deep learning. When the algorithm finds a breathing pattern corresponding to, or matching, one of the breathing patterns in the case of a fall in the database, the presence detection module 12 recognizes and detects a fall and alerts the user to fall detection. It will be appreciated that any suitable algorithms and methods may be employed for fall detection. Yet, in other examples, the presence detection module 12 may employ both thermal module 126 and radar module 123, analyzing thermal images and breathing patterns, comparing them with a database, and identifying falls of occupants in a space. In some implementations, referring to FIG. 2A, the display interface 41 may be configured to represent fall detection with respect to the monitored space 60. The display interface 41 may represent occupants' fall detection and their relative locations in the space 60. It will be appreciated that other suitable methods may be employed to represent fall detection.

The detection system 10 communicates occupancy information, including, but not limited to, loitering information, crowding information, line crossing detection, flow counting, cell phone/smartphone detection, and fall detection, with the main system 20 in terms of monitored spaces 60 by a network connection 30. The main system 20 receives the occupancy information from the detection system 10 and transmits the information to the visualization system 40 in order for the visualization system 40 to represent the occupancy information on the display interface 41, and the user of the system 1 can understand and be aware of the occupancy information about the monitored space 60 and make a decision or take action, e.g., dispatching security personnel to the monitored space 60.

As such, the visualization system 40 enables the user of the system 1 to effectively monitor and ensure health and safety in the establishment 70.

Figure 11:
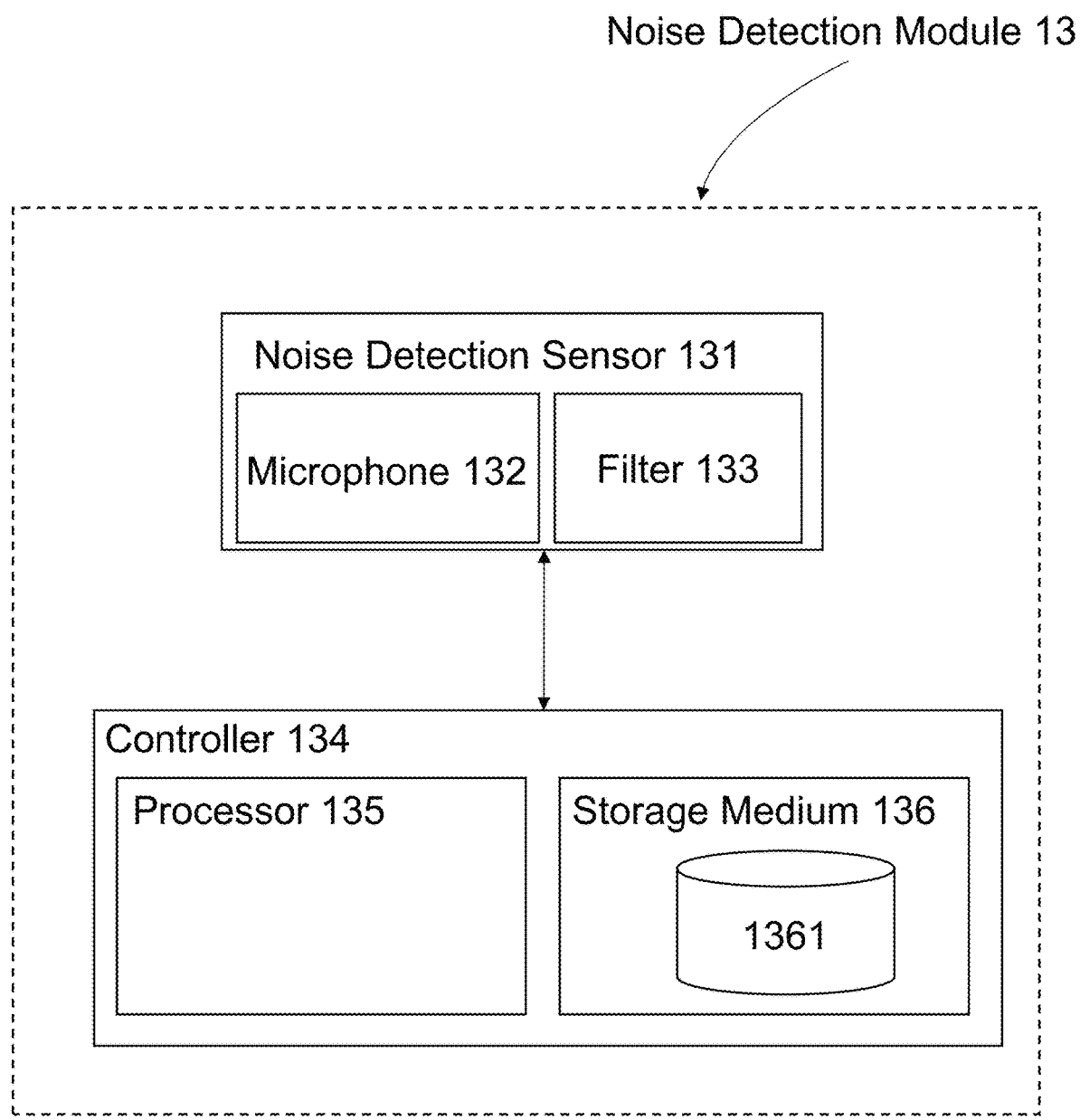
FIG. 11 shows a schematic representation of a noise detection module of the detection system of FIG. 4, according to an example embodiment of the present disclosure.

Referring to FIGS. 4 and 11, in some implementations, the detection system 10 may include a noise detection module 13 configured to monitor and detect audio signals, i.e., sounds, emitted from a monitored space 60. The noise detection module 13 may include a noise detection sensor 131 and a controller 134. The noise detection sensor 131 may include one or more microphones 132 to receive audio signals emitting from the monitored space 60 and a filter 133, which may include a hardware filter or software filter or both. In some implementations, the noise detection sensor 131 may include microphone(s) 132, i.e., four microphones. The controller 134 may include a processor 135 and a storage medium 136. The processor 135 may receive audio signals from the noise detection sensor 131 and process the signals via execution of instructions. The storage medium 136 may include a readable and writable storage medium communicatively coupled to the processor 135 and storing instructions that are executable by the processor 135. In some implementations, the controller 11 may function as a controller for the noise detection module 13, individually or in concert with the controller 134, and thus be configured to support and control the noise detection module 13. By processing audio signals, the noise detection module 13 produces noise information. The noise detection module 13 may include a database 1361 in the storage medium 136, and the database 1361 may include predetermined audio signals, including, but not limited to, screaming, shouting, glass breaking sounds, gunshots, tamper sounds, or keywords, including emergency keywords (e.g., "Help Me" and "Emergency"), and other noise anomalies. For example, when the noise detection module 13 detects an audio signal from the monitored space 60, the noise detection module 13 may compare the detected audio signal with sounds in the database 1361. In some implementations, the main system 20 may include such a database in the storage medium 22 (FIG. 1), and the main system 20 may compare the detected audio signal with sounds in the database in the storage medium 22. Yet, in some implementations, the noise detection module 13 may, in concert with the main system 20, compare the detected audio signal with the database 1361 and/or the database in the storage medium 22. The noise detection module 13 may employ algorithms utilizing artificial intelligence (AI), including machine learning and/or deep learning, in comparing the detected audio signal with the database 1361 and/or the database in the storage medium 22. It will be appreciated that other methods may be employed in determining a match case. In some implementations, the user of the system 1 may store predetermined audio signals, including predetermined key words by uploading, e.g., through a web application or a storage medium (e.g., a flash drive or an SD card), a file containing the predetermined audio signals onto the detection system 10 and storing the predetermined audio signals in the database 1361. Yet, in other implementations, the user may store predetermined audio signals by uploading, e.g., through a web application, a file containing the predetermined audio signals onto the main system 20 and storing the predetermined audio signals in the database in the storage medium 22. Such a file may include a keyword AI model. Such predetermined audio signals may include, but are not limited to, predetermined keywords in various languages. In some implementations, predetermined audio signals may be updated through the web application and stored in the database 1361 and/or the database in the storage medium 22. It will be appreciated that other methods of providing predetermined audio signals may be employed.

In some implementations, if there is noise information corresponding to the database 1361, e.g., "Help Me," referring to FIGS. 1 and 2A, the detection system 10 transmits the noise information to the main system 20, and the visualization system 40 represents the detected noise information through the display interface 41 in order for the user of the system 1 to respond to the detection so as to ensure safety and health in the establishment 70. In other implementations, detection of screaming, shouting, glass breaking sounds, gunshots, and/or tamper sounds may be represented by the visualization system 40 on the portion 413 on the display terminal 41. Yet, in other implementations, detection of keywords, set by the user of the system 1, may be represented on the portion 414 on the display terminal 41. It will be appreciated that other methods may be employed to represent such detection on the display interface 41. In some implementations, the alert system 50 may notify the user of the system 1 of the detected sound, e.g., "Help Me," and the system 1 may dispatch security personnel to the monitored space 60. In other implementations, the noise module 13 may be configured to detect sounds exceeding a certain noise level (dB) threshold, e.g., extremely loud noise, set by the user or a default setting. The alert system 50 may then send out such detection to the user so that the user can respond to and control it.

Figure 12:
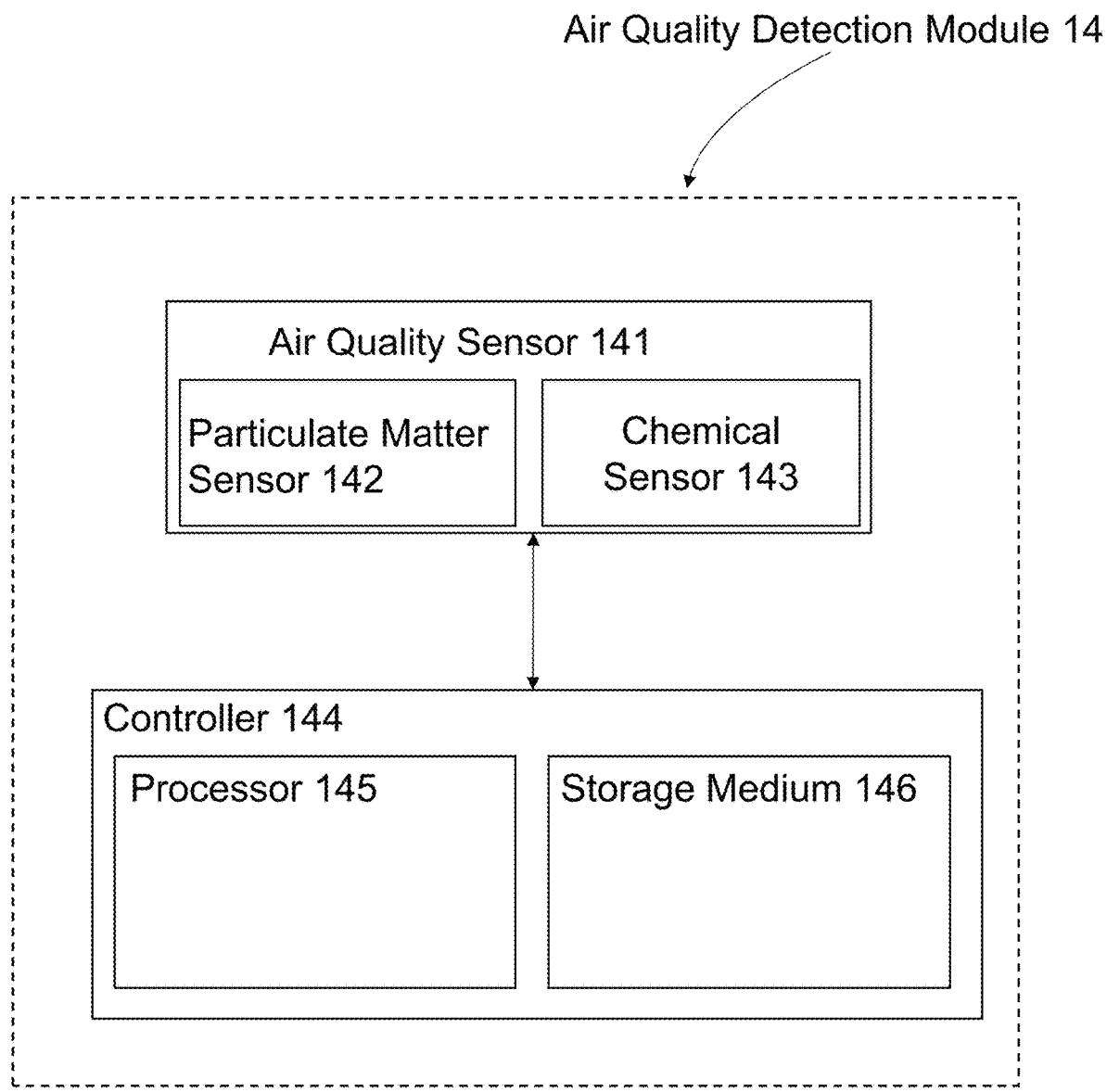
FIG. 12 shows a schematic representation of an air quality detection module of the detection system of FIG. 4, according to an example embodiment of the present disclosure.

Referring to FIGS. 4 and 12, in some implementations, the detection system 10 may include an air quality detection module 14. The air quality detection module 14 may be configured to detect particulate matter or airborne chemicals in a monitored space 60, and such particle matter or airborne chemicals may include, but are not limited to, aerosol generated by vaping, tetrahydrocannabinol (THC), cigarette, volatile organic compounds, formaldehyde, and smoke. The air quality detection module 14 may include an air quality sensor 141 and a controller 144. The air quality sensor 141 may include a particulate matter sensor 142 configured to detect particulate matter in the monitored space 60 and a chemical sensor 143 configured to detect airborne chemicals in the monitored space 60. The controller 144 may include a processor 145 and a storage medium 146. The processor 145 may receive signals from the air quality sensor 141 and process the signals via execution of instructions. The storage medium 146 may include a readable and writable storage medium communicatively coupled to the processor 145 and storing instructions that are executable by the processor 145. For example, a particulate matter sensor 142 may employ laser scattering technology, and vape aerosols suspended in the air may deflect light in the sensor 142, and the sensor 142 may compare such deflection with data (not shown), and the air quality module 14 may detect vaping in the space 60. The chemical sensor 143 may measure concentrations of certain airborne chemicals in the monitored space 60 and may send an alert if the concentrations of the chemicals exceed a threshold. It will be appreciated that other methods may be employed to detect particulate matter or airborne chemicals. In some implementations, the controller 11 may function as a controller for the air quality detection module 14, individually or in concert with the controller 144, and thus be configured to support and control the air quality detection module 14. In some implementations, the detection system 10 may send detection of particulate matter or chemicals in the monitored space 60, e.g., vaping, tetrahydrocannabinol (THC), or masking, to the main system 20, and, referring to FIG. 2A, the visualization system 40 may represent such detection on the display terminal 41, e.g., vaping 413, THC 413, or masking 413, in the monitored space 60. In some implementations, the user of the system 1 may define masking as the detection of a substance in the air other than aerosol generated by vaping, THC, and nicotine. Such detection may include the use of aerosol sprays, including, but not limited to, deodorant and Lysol. In some implementations, the alert system 50 may notify the user of the system 1 of such detection, and the user of the system 1 may take action to address, mitigate, or remove the detected unwanted behaviors and/or undesirable conditions, e.g., dispatching security personnel to the monitored space 60 to stop vaping in the space 60.

In some implementations, if the air quality detection module 14 detects such particulate matter or chemicals, referring to FIGS. 1, 2A and 2B, the visualization system 40 may represent such detection and in which monitored spaces 60 it detected. An air quality detection module 14 may further be configured to measure the temperature of the air in a space 60 and the air quality in the space 60, including, but not limited to, an air quality index (AQI) and total volatile organic compounds (TVOC). The visualization system 40 may represent such air quality in numbers and colors on the display interface 41 on, e.g., a portion 414. The higher the AQI value is, the greater the level of air pollution and the greater the health concern exists. An AQI value may be represented with a different quality indicator, e.g., a value from 0 to 50 with "Good" in green, a value from 51 to 100 with "Moderate" in yellow, a value from 101 to 150 with "Unhealthy for Sensitive Groups" in orange, a value from 151 to 200 with "Unhealthy" in red, a value from 201 to 300 with "Very Unhealthy" in purple, and a value from 301 to 500 with "Hazardous" in maroon. For example, an AQI value, e.g., 27, may be represented with a quality indicator, such as "Good" in green, on, e.g., the portion 414. An AQI value, e.g., 301 or higher, may be represented with a quality indicator, such as "Hazardous" in maroon, on, e.g., the portion 414. It will be appreciated that other methods may be employed to represent an AQI value. TVOC may be represented as a number, e.g., 27, in parts per billion (ppb), or in some implementations, milligrams per cubic meter ($mg/m^3$) or micrograms per cubic meter ($\mu g/m^3$), with a quality indicator, e.g., a color, green denoting good and a different color denoting different quality. The temperature may be represented in Celsius or Fahrenheit, or both, on, e.g., the portion 414. It will be appreciated that other methods may be employed to represent the air quality in a monitored space 60. The visualization system 40 may further represent overall health information about a monitored space 60 as a different value, such as a Health Index, on, e.g., the portion 414, which may take into account various factors, such as AQI, TVOC, and temperature, and may be represented as a number between 0 and 100, with a number from 0 to 59 denoting bad, a number from 60 to 79 denoting poor, a number from 80 to 89 denoting moderate, and a number from 90 to 100 denoting good. A Health Index may use a weighted average of a few metrics. In some implementations, a color may be employed to represent a Health Index, such as green denoting good and red denoting bad. A Health Index value, for example 90, may be represented with a quality indicator, such as "Good" in green, on e.g., the portion 414. In some implementations, a Health Index may be represented in a level (FIG. 2B), each level denoting a different range of Health Index values. Each Health Index Level may correspond to a different set of Health Index, e.g., Health Index Level 1 corresponds to good, Health Index Level 2 corresponds to moderate, Health Index Level 3 corresponds to poor, and Health Index Level 4 corresponds to bad. It will be appreciated that other measures and methods may be employed to display the overall health information. In some implementations, a Risk Level may be represented on, e.g., the portion 414. A Risk Level may be a calculated value, taking into account measured amounts of certain chemicals in the monitored space 60, e.g., concentrations, and use a weighted average of a few metrics. A Risk Level may be represented with a different quality indicator, e.g., a value from 10 to 20 with "Good" in green, a value from 21 to 30 with "Fine," a value from 31 to 40 with "Bad," and a value from 41 to 50 with "Dangerous." "Good" may denote a low-risk level in the monitored space 60, and "Dangerous" may denote a high-risk level. "Fine" may denote a relatively low-risk level but higher than that of "Good," while "Bad" denotes a risk level relatively lower than that of "Dangerous" but still higher than that of "Fine." For example, Risk Level 17 may indicate Good in green. It will be appreciated that other methods may be employed to represent a Risk Level. An alert system 50 may also notify the user of the system 1 of such detection.

In some implementations, the detection system 10 may be deployed in a monitored space 60 or in the vicinity of the space 60, and the main system 20 may be deployed remotely, connected to the detection system 10 by a network connection 30. The detection system 10 sends occupancy information to the visualization system 40 by the network connection 30, and the network connection 30 may be electrical contacts, e.g., wires, or wired or wireless network connections. In some implementations, wired or wireless network connections may relay information associated with an application programming interface (API) request or call, a transmission control protocol (TCP), a hypertext transfer protocol (HTTP), a hypertext transfer protocol secure (HTTPS), or a message queuing telemetry transport (MQTT) protocol or a secure variant of the MQTT protocol (MQTTS), or combinations thereof. It will be appreciated that any other suitable methods or protocols may be employed.

Referring back to FIG. 4, in some implementations, the detection system 10 may include a power management module 15. The detection system 10 may consume low power or be energy efficient, and the power management module 15 may run the detection system 10 on battery power. With the detection system 10 running on battery power, the user of the system 1 may install the detection system 10 at locations without being bound by the location of power outlet. In other implementations, the power management module 15 may employ the power over ethernet (POE) standard, and the detection system 10 may supply electricity through network cables without separate power cables connected to power outlets. In some implementations, a daisy chain configuration may be employed utilizing PoE, e.g., four device PoE daisy chain. Daisy chaining of multiple detection systems 10 may save time and cables during installation. It will be appreciated that other methods, configurations, and arrangements may be employed for power management.

Referring back to FIG. 1, the visualization system 40 may be configured to as a cloud management platform or network-based management platform. In the case of a cloud management platform, the detection system 10 may send information to the main system 20, part of which is running on cloud. In the case of a network-based management platform, a user may construct an internal network on site 70, e.g., establishments or buildings, and the detection system 10 and the main system 20 may locate on site. In some implementations, to enhance security of the system 1, the system 1 may be implemented on an air-gapped network in which an internal network is completely isolated from the outer Internet with no inbound or outbound traffic.

In some implementations, visualization may be achieved by real-time streaming of occupancy information about the monitored space 60, and the visualization system 40 may provide the occupancy information in real time to the user, and the user can track the information in real time and will be better informed. The detection system 10 may be configured to monitor and detect the presence in real time and transmit occupancy information, including, but not limited to, loitering and crowding information, to the main system 20, and the visualization system 40 may process the received occupancy information and transmit the occupancy information by using a streaming protocol. The streaming protocol may employ the real-time streaming protocol (RTSP) or the open network video interface forum (ONVIF) standard, or both. In some implementations, the streaming protocol may include other protocols, but is not limited to, hypertext markup language (HTML), cascading style sheets (CSS), JavaScript, PHP: hypertext preprocessor (PHP), or combinations thereof, in visualizing occupancy information and/or detected unwanted behaviors or undesirable conditions on a web-based display interface 41. It will be appreciated that any other suitable methods or protocols may be employed.

In some implementations, the health and safety monitoring and alert system 1 may include an alert system 50, and the alert system 50 may provide occupancy information to a user of the system 1 by electronic transmission, such as a text message, a mobile application push notification, email, and combinations thereof. It will be appreciated that other methods of electronic transmission may be employed. For example, when the system 1 detects and monitors the presence of an occupant 80 in a monitored space 60, the system 1 may send out such detection to the user in accordance with the rules the user set or a default setting. The system 1 may send an alert to the user periodically, e.g., every ten minutes, or the system 1 may send an alert when there is a person remaining in the space 60 more than a certain duration, e.g., eight minutes, or the system 1 may send an alert when there are more than a certain number, e.g., five persons in the space 60. It will be appreciated that users of the system may set different rules to receive an alert, and different rules and methods may be employed. In some implementations, the alert system 50 may communicate with a third-party system with respect to certain detection in accordance with the rules the user set or a default setting. For example, the alert system 50 may communicate detection of, e.g., a gunshot with a third-party system through an API request or call, TCP, HTTP, HTTPS, MQTT or MQTTS, or combinations thereof. The alert system 50 may trigger the third-party system to take action in response, such as activating alarms, flashing warning lights, and/or closing doors to lock the monitored spaces to ensure safety in the establishment. In some implementations, the system 1 may send log data of the detection system 10 to the user in accordance with the rules the user set or a default setting. The log data may include, but is not limited to, records of all the events occurring in the detection system 10 and checking whether the detection system 10 is functioning properly. The system 1 may send log data to the user periodically. It will be appreciated that users of the system may set different rules to receive log data, and different rules and methods may be employed.

Figure 13:
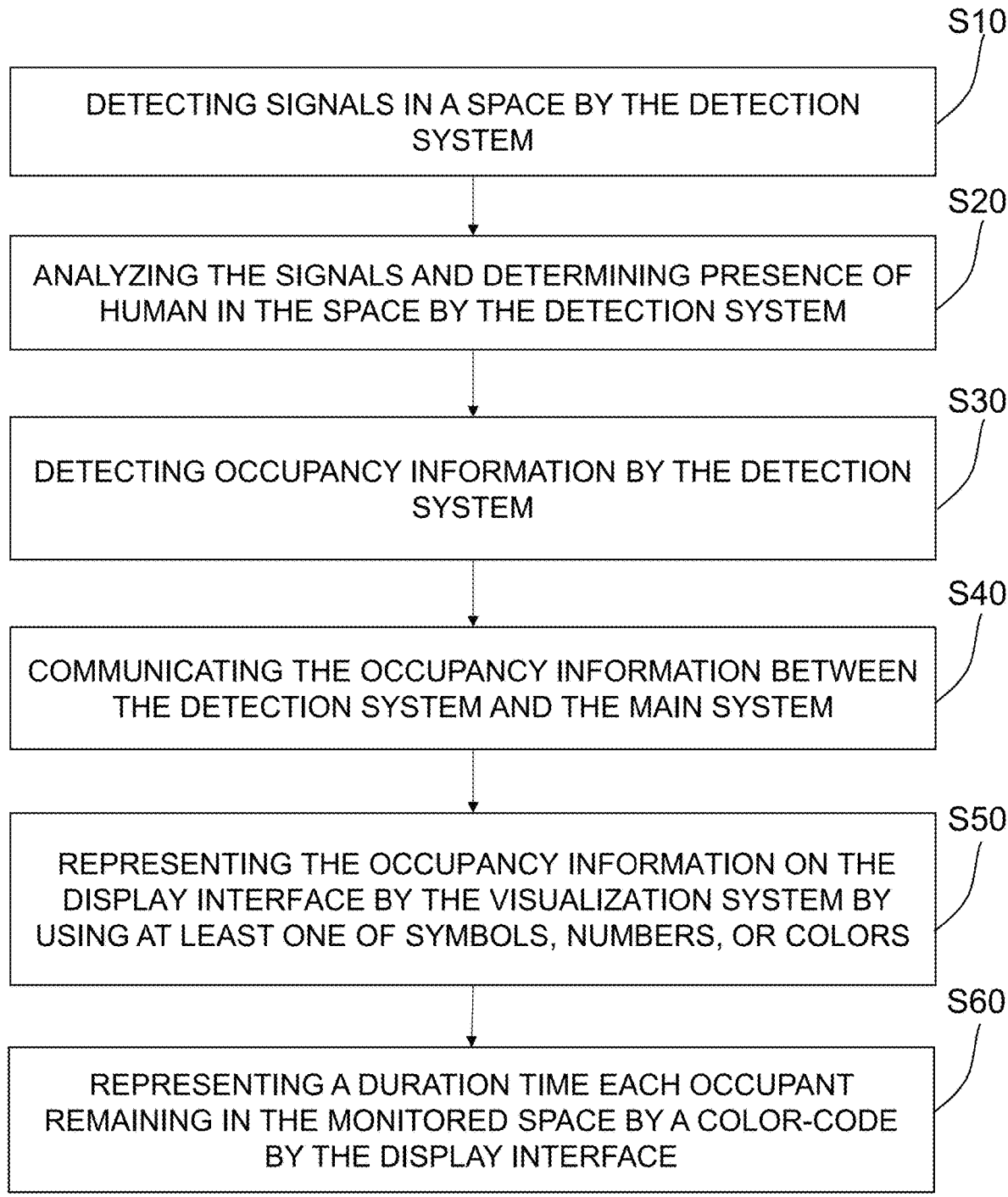
FIG. 13 shows a flowchart illustrating an exemplary method of monitoring health and safety information of a space in a privacy compliant manner, according to an example embodiment of the present disclosure.

In monitoring health and safety information of a space in a privacy compliant manner, a health and safety monitoring and alert system 1 may include a detection system 10 and a main system 20. The detection system 10 may include a presence detection module 12. The main system 20 may include a visualization system 40 including a display interface 41. Referring to FIG. 13, in step S10, the detection system 10 may detect signals in a space 60. In some implementations, the presence detection module 12 may comprise a radar module 123, and the radar module 123 may emit signals, detect reflections of the emitted signals from multiple objects in the space 60, analyze the detected reflections, determine the presence and movement of occupants 80 in the space 60, and detect occupancy information. In step S20, the detection system 10 may analyze the signals and determine presence of a human in the space 60. In step S30, the detection system 10 may detect occupancy information. In step S40, the detection system 10 and the main system 20 may communicate the occupancy information. The occupancy information may include one or more of (i) a number of occupants in the monitored space; (ii) a duration time of each occupant remaining in the monitored space; (iii) a location of each occupant being located in the monitored space; (iv) entrance of an occupant into the monitored space; (v) a departure of an occupant from the monitored space; (vi) a number of occupants entered into the monitored space; (vii) a number of occupants exiting the monitored space; and (viii) an average number of occupants in the monitored space in a certain time range. In step S50, the visualization system 40 may represent the occupancy information on the display interface by using at least one of symbols, numbers, or colors in a privacy compliant manner. In some implementations, the visualization system 40 may represent the occupancy information by using a streaming protocol, the streaming protocol employing the real-time streaming protocol (RTSP) or the open network video interface forum (ONVIF) standard, or both. In some implementations, the streaming protocol may include other protocols, but is not limited to, hypertext markup language (HTML), cascading style sheets (CSS), JavaScript, PHP: hypertext preprocessor (PHP), or combinations thereof, in visualizing the occupancy information. Additionally, in some implementations, if the occupancy information includes how long occupants remain in the monitored space 60, i.e., a duration time each occupant remaining in the monitored space 60, in step S60, the display interface 41 may represent the duration time each occupant remaining in the monitored space 60 by a color-code.

While the invention has been described with reference to a preferred embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

We claim:

1. A method of monitoring health and safety information of a space, the method comprising:
providing a detection system including a presence detection module and a main system including a visualization system including a display interface;
detecting signals in a space by the detection system;
analyzing the signals and determining presence of a human in the space by the detection system;
detecting occupancy information by the detection system, the occupancy information including one or more of:
(i) a number of occupants in the monitored space;
(ii) a duration time of each occupant remaining in the monitored space;
(iii) a location of each occupant being located in the monitored space;
(iv) entrance of an occupant into the monitored space;
(v) a departure of an occupant from the monitored space;
(vi) a number of occupants entered into the monitored space;
(vii) a number of occupants exiting the monitored space; and
(viii) an average number of occupants in the monitored space in a certain time range;
communicating the occupancy information between the detection system and the main system; and
representing, by the visualization system, the occupancy information on the display interface by using at least one of symbols, numbers, or colors.

2. The method according to claim 1, wherein the display interface represents the duration time each occupant remains in the monitored space by a color-code.

3. The method according to claim 1, wherein the visualization system represents the occupancy information by using a streaming protocol, the streaming protocol employing one or more of a real-time streaming protocol (RTSP), an open network video interface forum (ONVIF) standard, hypertext markup language (HTML), cascading style sheets (CSS), JavaScript, PHP: hypertext preprocessor (PHP), or combinations thereof.

4. The method according to claim 1, wherein the presence detection module comprises a radar module, and the radar module emits signals, detects reflections of the emitted signals from multiple objects in the space, analyzes the detected reflections, determines the presence and movement of occupants in the space, and detects occupancy information, and wherein the radar module detects heartbeat or respiration, or both.

5. The method according to claim 1, wherein the presence detection module comprises a thermal module, the thermal module is configured to detect heat emitted by objects, analyzes the detected heat and temperature variations caused by human presence, determines the presence and movement of occupants in the space, and detects occupancy information.

6. The method according to claim 1, wherein the presence detection module comprises at least i) a thermal module configured to trace an occupant in the monitored space and compare a posture of the occupant with postures in a database, the database including various postures, including postures of standing positions, postures of lying positions, and postures of sleeping positions, and ii) a radar module configured to detect micro-tremors such that the radar module can distinguish occupants from objects in the monitored space, analyze occupants' breathing rates, and compare the breathing patterns with breathing patterns in a database.

7. The method according to claim 6, wherein the thermal module identifies the posture of an occupant in the monitored space and compares the posture with the postures of lying positions in the database, and the radar module detects the breathing pattern of the occupant and compares the breathing pattern with breathing patterns in the case of a fall stored in the database, whereby the presence detection module detects a fall of the occupant.

8. The method according to claim 1, wherein the presence detection module comprises a Bluetooth module, the Bluetooth module being configured to detect Bluetooth signals from mobile devices, analyze the detected Bluetooth signals, and determine the number of mobile devices within a monitored space.

9. The method according to claim 1 further comprising providing the occupancy information by electronic transmission selected from the group consisting of a text message, a mobile application push notification, an email, and combinations thereof.

10. The method according to claim 1, wherein the detection system comprises a noise detection module, the noise detection module detects audio signals emitted from the space, processes the detected audio signals, produces noise information, and analyzes the noise information by comparing with information in a database, the detection system transmits the noise information corresponding to the database to the main system, and the method further comprises communicating the noise information between the detection system and the main system and representing, by the visualization system, the noise information on the display by using at least one of symbols, numbers, or colors.

11. The method according to claim 10, wherein the database comprises at least one of screaming, shouting, glass breaking sounds, gunshots, tamper sounds, predetermined words, or emergency keywords.

12. The method according to claim 1, wherein the detection system comprises an air quality detection module, the air quality detection module detects predetermined particulate matter or airborne chemicals in the space, the detection system transmits detection of the predetermined particulate matter or airborne chemicals in the space to the main system, and the method further comprises communicating the detection of the predetermined particulate matter or airborne chemicals between the detection system and the main system and representing, by the visualization system, such detection on the display by using at least one of symbols, numbers, or colors.

13. The method according to claim 12, wherein the predetermined particulate matter or airborne chemicals comprise at least one of vape aerosols, tetrahydrocannabinol (THC), chemical components of cigarette smoke, or volatile organic.

14. A health and safety monitoring and alert system comprising:
a main system including:
a processor configured to communicate health and safety information relating to occupants in a space;
a readable and writable storage medium communicatively coupled to the processor and storing instructions that are executable by the processor; and
a visualization system configured to communicate with the processor, the visualization system including a display interface; and
a detection system including:
a controller coupled to a module configured to detect health and safety information relating to occupants in a space, the controller including a controller processor and a readable and writeable controller storage medium communicatively coupled to the controller processor and storing instructions that are executable by the controller processor, the module including a presence detection module configured to detect human presence in the space;
wherein the display interface is configured to represent the detected health and safety information by using at least one of symbols, numbers, or colors, the health and safety information including occupancy information, the occupancy information including one or more of:
(i) a number of occupants in the monitored space;
(ii) a duration time of each occupant remaining in the monitored space;
(iii) a location of each occupant being located in the monitored space;
(iv) entrance of an occupant into the monitored space;
(v) a departure of an occupant from the monitored space;
(vi) a number of occupants entered into the monitored space;
(vii) a number of occupants exiting the monitored space; and
(viii) an average number of occupants in the monitored space in a certain time range; and
wherein the detection system is configured to communicate the detected health and safety information with the main system by a network connection.

15. The health and safety monitoring and alert system according to claim 14, wherein the presence detection module comprises a radar module, and the radar module is configured to emit signals, detect reflections of the emitted signals from multiple objects in the space, analyze the detected reflections and determine the presence and movement of occupants in the space, and detects occupancy information, and wherein the radar module is configured to use millimeter wave signals.

16. The health and safety monitoring and alert system according to claim 14, wherein the presence detection module comprises a thermal module, and the thermal module is configured to detect heat emitted by objects, analyze the detected heat and temperature variations caused by human presence, determine the presence and movement of occupants in the space, and detect occupancy information.

17. The health and safety monitoring and alert system according to claim 14, wherein the presence detection module comprises at least i) a thermal module configured to trace an occupant in the monitored space and compare a posture of the occupant with postures in a database, the database including various postures, including postures of standing positions, postures of lying positions, and postures of sleeping positions, and ii) a radar module configured to detect micro-tremors such that the radar module can distinguish occupants from objects in the monitored space, analyze occupants' breathing rates, and compare the breathing patterns with breathing patterns in a database.

18. The health and safety monitoring and alert system according to claim 17, wherein the thermal module identifies the posture of an occupant in the monitored space and compares the posture with the postures of lying positions in the database, and the radar module detects the breathing pattern of the occupant and compares the breathing pattern with breathing patterns in the case of a fall stored in the database, whereby the presence detection module detects a fall of the occupant.

19. The health and safety monitoring and alert system according to claim 14, wherein the presence detection module comprises a Bluetooth module, the Bluetooth module being configured to detect Bluetooth signals from mobile devices, analyze the detected Bluetooth signals, and determine the number of mobile devices within a monitored space.

20. The health and safety monitoring and alert system according to claim 14, wherein the detection system further comprises a noise detection module, and the noise detection module includes a microphone configured to detect predetermined sounds in the space and a filter.

21. The health and safety monitoring and alert system according to claim 20, wherein the predetermined sounds comprise at least one of screaming, shouting, glass breaking sounds, gunshots, tamper sounds, words, or emergency keywords.

22. The health and safety monitoring and alert system according to claim 14, wherein the detection system further comprises an air quality detection module, the air quality detection module is configured to detect predetermined particulate matter or airborne chemicals in the space, the health and safety information includes detection of the predetermined particulate matter or airborne chemicals in the space, and the display interface is configured to represent one or more of vaping, tetrahydrocannabinol (THC), smoke, or volatile organic compounds.

23. The health and safety monitoring and alert system according to claim 14, wherein the system further comprising an alert system providing the health and safety information to a user of the system by electronic transmission selected from the group consisting of a text message, a mobile application push notification, email, and combinations thereof.

24. A health and safety monitoring and alert system comprising:
  a main system including:
  a processor configured to communicate health and safety information relating to occupants in a space;
  a readable and writable storage medium communicatively coupled to the processor and storing instructions that are executable by the processor; and
  a visualization system configured to communicate with the processor, the visualization system including a display interface; and
  a detection system including:
  a controller coupled to a module configured to detect health and safety information relating to occupants in a space, the controller including a controller processor and a readable and writeable controller storage medium communicatively coupled to the controller processor and storing instructions that are executable by the controller processor, the module including:
  (i) a presence detection module configured to detect presence of occupants in the space, wherein the presence detection module comprises a thermal module configured to detect heat emitted by the occupants in order to obtain occupancy information, the occupancy information including one or more of: a number of occupants in the monitored space; a duration time of each occupant remaining in the monitored space; and a location of each occupant being located in the monitored space;
  (ii) a noise detection module including a microphone configured to detect predetermined sounds in the space and a filter, wherein the predetermined sounds comprise at least one of screaming, shouting, glass breaking sounds, gunshots, tamper sounds, words, or emergency keywords; and
  (iii) an air quality detection module configured to detect predetermined particulate matter or airborne chemicals in the space;
  wherein the display interface is configured to represent the detected health and safety information by using at least one of symbols, numbers, or colors; and
  wherein the detection system is configured to communicate the detected health and safety information with the main system by a network connection.

25. The health and safety monitoring and alert system according to claim 24, wherein the thermal module is configured to trace an occupant in the monitored space and compare a posture of the occupant with postures in a database, the database including various postures, the various postures including postures of standing positions, postures of lying positions, and postures of sleeping positions, and wherein the thermal module identifies the posture of an occupant in the monitored space and compares the posture with the postures of lying positions in the database, whereby the presence detection module detects a fall of the occupant.

26. The health and safety monitoring and alert system according to claim 24, wherein the health and safety information includes detection of the predetermined particulate matter or airborne chemicals in the space, and the display interface is configured to represent one or more of vaping, tetrahydrocannabinol (THC), smoke, or volatile organic compounds.

27. A health and safety monitoring and alert system comprising:
  a main system including:
  a processor configured to communicate health and safety information relating to occupants in a space;
  a readable and writable storage medium communicatively coupled to the processor and storing instructions that are executable by the processor; and
  a visualization system configured to communicate with the processor, the visualization system including a display interface; and
  a detection system including:
  a controller coupled to a module configured to detect health and safety information relating to occupants in a space, the controller including a controller processor and a readable and writeable controller storage medium communicatively coupled to the controller processor and storing instructions that are executable by the controller processor, the module including:
  (i) a presence detection module configured to detect presence of occupants in the space, wherein the presence detection module comprises a Bluetooth module configured to detect Bluetooth signals from mobile devices in order to obtain occupancy information, the occupancy information including one or more of: a number of occupants in the monitored space; a duration time of each occupant remaining in the monitored space; and a location of each occupant being located in the monitored space;
  (ii) a noise detection module including a microphone configured to detect predetermined sounds in the space and a filter, wherein the predetermined sounds comprise at least one of screaming, shouting, glass breaking sounds, gunshots, tamper sounds, words, or emergency keywords; and
  (iii) an air quality detection module configured to detect predetermined particulate matter or airborne chemicals in the space;
  wherein the display interface is configured to represent the detected health and safety information by using at least one of symbols, numbers, or colors; and
  wherein the detection system is configured to communicate the detected health and safety information with the main system by a network connection.

28. The health and safety monitoring and alert system according to claim 27, wherein the presence detection module further comprises a radar module, and the radar module is configured to emit signals, detect reflections of the emitted signals from multiple objects in the space, analyze the detected reflections and determine the presence and movement of occupants in the space, and detects occupancy information, and wherein the radar module is configured to use millimeter wave signals.

29. The health and safety monitoring and alert system according to claim 28, wherein the presence detection module further comprises i) a thermal module configured to detect heat emitted by objects, analyze the detected heat and temperature variations caused by presence of occupants, determine the presence and movement of occupants in the space, trace an occupant in the monitored space, and compare a posture of the occupant with postures in a database, the database including various postures, the various postures including postures of standing positions, postures of lying positions, and postures of sleeping positions, and ii) the radar module configured to detect micro-tremors such that the radar module can distinguish occupants from objects in the monitored space, analyze occupants' breathing rates, and compare the breathing patterns with breathing patterns in a database, and wherein the thermal module identifies the posture of an occupant in the monitored space and compares the posture with the postures of lying positions in the database, and the radar module detects the breathing pattern of the occupant and compares the breathing pattern with breathing patterns in the case of a fall stored in the database, whereby the presence detection module detects a fall of the occupant.

30. The health and safety monitoring and alert system according to claim 27, wherein the health and safety information includes detection of the predetermined particulate matter or airborne chemicals in the space, and the display interface is configured to represent one or more of vaping, tetrahydrocannabinol (THC), smoke, or volatile organic compounds.

* * * * *